United States Patent
Ranu

(10) Patent No.: US 9,327,128 B2
(45) Date of Patent: May 3, 2016

(54) AUTOMATIC ANODE AND CATHODE FRACTIONAL CONTROL AND LOCATION TO SELECTIVELY AVOID DORSAL ROOT STIMULATION

(71) Applicant: Boston Scientific Neuromodulation Corporation, Valencia, CA (US)

(72) Inventor: Emarit A. S. Ranu, Fort Collins, CO (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 0 days.

(21) Appl. No.: 14/526,031

(22) Filed: Oct. 28, 2014

(65) Prior Publication Data

US 2015/0119957 A1    Apr. 30, 2015

Related U.S. Application Data

(60) Provisional application No. 61/897,739, filed on Oct. 30, 2013.

(51) Int. Cl.
*A61N 1/00* (2006.01)
*A61N 1/36* (2006.01)
(Continued)

(52) U.S. Cl.
CPC .......... *A61N 1/36185* (2013.01); *A61N 1/0553* (2013.01); *A61N 1/3605* (2013.01); *A61N 1/37247* (2013.01); *A61N 2001/34* (2013.01)

(58) Field of Classification Search
CPC ............ A61N 1/36185; A61N 1/3605; A61N 1/0553; A61N 1/37247
USPC .......................................................... 607/59
See application file for complete search history.

(56) References Cited

U.S. PATENT DOCUMENTS 5,938,690 A    8/1999  Law et al.
5,941,906 A    8/1999  Barreras, Sr. et al.
(Continued)

FOREIGN PATENT DOCUMENTS

JP    2011529378 A    12/2011
JP    2013537090 A     9/2013
(Continued)

OTHER PUBLICATIONS

"International Application Serial No. PCT/US2014/062663, International Search Report mailed Jan. 23, 2015", 6 pgs.
(Continued)

*Primary Examiner* — Robert N Wieland
(74) *Attorney, Agent, or Firm* — Schwegman Lundberg & Woessner, P.A.

(57) ABSTRACT

A therapeutic neurostimulation system configured for providing therapy to a patient. The neurostimulation system comprises a neurostimulation lead having an array of electrodes arranged along a longitudinal axis configured for being implanted along a spinal cord of a patient, a neurostimulation device configured for delivering electrical stimulation energy to active ones of the electrode array, and control/processing circuitry for instructing the neurostimulation device to configure an active electrode as a cathode, and two active electrodes longitudinally flanking and laterally offset from the cathode as anodes, selecting a ratio of stimulation amplitude values for the two anodes based on a known longitudinal location of the implanted neurostimulation lead relative to the spinal cord, and instructing the neurostimulation device to distribute the electrical stimulation energy between the two anodes in accordance with the selected stimulation amplitude value ratio.

20 Claims, 17 Drawing Sheets

(51) Int. Cl.
*A61N 1/372* (2006.01)
*A61N 1/05* (2006.01)
*A61N 1/34* (2006.01)

(56) References Cited

U.S. PATENT DOCUMENTS

| | | |
|---|---|---|
| 6,516,227 B1 | 2/2003 | Meadows et al. |
| 6,675,046 B2 | 1/2004 | Holsheimer |
| 6,895,280 B2 | 5/2005 | Meadows et al. |
| 6,993,384 B2 | 1/2006 | Bradley et al. |
| 7,317,948 B1 | 1/2008 | King et al. |
| 7,333,857 B2 | 2/2008 | Campbell |
| 7,539,538 B2 | 5/2009 | Parramon et al. |
| 7,650,184 B2 | 1/2010 | Walter |
| 7,979,133 B2 | 7/2011 | Feler et al. |
| 7,987,000 B2 | 7/2011 | Moffitt et al. |
| 8,019,439 B2 | 9/2011 | Kuzma et al. |
| 8,160,328 B2 | 4/2012 | Goetz et al. |
| 8,180,129 B2 | 5/2012 | Goetz et al. |
| 8,224,453 B2 | 7/2012 | De Ridder |
| 8,255,057 B2 | 8/2012 | Fang et al. |
| 8,355,797 B2 | 1/2013 | Caparso et al. |
| 8,412,345 B2 | 4/2013 | Moffitt |
| 8,437,857 B2 | 5/2013 | Moffitt et al. |
| 8,455,716 B2 | 6/2013 | Huang et al. |
| 8,504,147 B2 | 8/2013 | Deem et al. |
| 8,594,797 B2 | 11/2013 | Lee |
| 8,615,300 B2 | 12/2013 | Feler et al. |
| 8,649,874 B2 | 2/2014 | Alataris et al. |
| 8,660,653 B2 | 2/2014 | Kothandaraman |
| 8,670,831 B2 | 3/2014 | Wacnik et al. |
| 8,676,329 B2 | 3/2014 | Wacnik et al. |
| 8,676,331 B2 | 3/2014 | Parker |
| 8,700,178 B2 | 4/2014 | Anderson |
| 8,731,675 B2 | 5/2014 | Ranu et al. |
| 8,751,009 B2 | 6/2014 | Wacnik |
| 2003/0139781 A1 | 7/2003 | Bradley et al. |
| 2004/0116978 A1 | 6/2004 | Bradley |
| 2007/0150036 A1 | 6/2007 | Anderson |
| 2008/0188909 A1 | 8/2008 | Bradley |
| 2009/0196472 A1 | 8/2009 | Goetz et al. |
| 2009/0198306 A1 | 8/2009 | Goetz et al. |
| 2009/0204173 A1 | 8/2009 | Fang et al. |
| 2009/0319013 A1 | 12/2009 | Boling et al. |
| 2010/0010566 A1 | 1/2010 | Thacker et al. |
| 2010/0057163 A1 | 3/2010 | Moffitt et al. |
| 2010/0121409 A1 | 5/2010 | Kothandaraman et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274317 A1 | 10/2010 | Parker et al. |
| 2010/0274318 A1 | 10/2010 | Walker et al. |
| 2010/0274326 A1 | 10/2010 | Chitre et al. |
| 2011/0282414 A1 | 11/2011 | Kothandaraman et al. |
| 2012/0059446 A1 | 3/2012 | Wallace et al. |
| 2012/0083709 A1 | 4/2012 | Parker et al. |
| 2012/0253422 A1 | 10/2012 | Thacker et al. |
| 2012/0265279 A1 | 10/2012 | Zhu |
| 2012/0283797 A1 | 11/2012 | De Ridder |
| 2012/0290041 A1 | 11/2012 | Kim et al. |
| 2013/0066411 A1 | 3/2013 | Thacker et al. |
| 2013/0096644 A1 | 4/2013 | Fang et al. |
| 2013/0116752 A1 | 5/2013 | Parker et al. |
| 2013/0268021 A1 | 10/2013 | Moffitt |
| 2013/0296975 A1 | 11/2013 | Lee et al. |
| 2014/0081349 A1 | 3/2014 | Lee et al. |
| 2014/0277267 A1 | 9/2014 | Vansickle et al. |
| 2015/0012068 A1* | 1/2015 | Bradley et al. ............... 607/62 |

FOREIGN PATENT DOCUMENTS

| | | |
|---|---|---|
| WO | WO-2006029257 A2 | 3/2006 |
| WO | WO-2006135791 A2 | 12/2006 |
| WO | WO-2015066033 A1 | 5/2015 |

OTHER PUBLICATIONS

"International Application Serial No. PCT/US2014/062663, Written Opinion mailed Jan. 23, 2015", 9 pgs.

Kothandaraman, Sridhar, et al., "System and Method for Connecting Devicesto a Neurostimulator", U.S. Appl. No. 61/694,695, filed Aug. 29, 2012.

Lee, Dongchul, "Neurostimulation System for Defining a Generalized Ideal Multipole Configuration", U.S. Appl. No. 61/452,965, filed Mar. 15, 2011.

Vansickle, Dennis Allen, et al., "Neuromodulation System and Method for Transitioning Between Programming Modes", U.S. Appl. No. 14/214,752, filed Mar. 15, 2014.

Rao, Prakash, et al., "Technique for Linking Electrodes Together During Programming of Neurostimulation System", U.S. Appl. No. 61/561,760, filed Nov. 18, 2011.

* cited by examiner

| Longitudinal location of neurostimulation lead | Ratio of stimulation amplitudes of longitudinal anodes |
|---|---|
| Vertebrae C1- C7 | 1:1 |
| Vertebrae T1-T12 | 2:1 |
| Vertebrae L1-L5 | 4:1 |

FIG. 9

AUTOMATIC ANODE AND CATHODE FRACTIONAL CONTROL AND LOCATION TO SELECTIVELY AVOID DORSAL ROOT STIMULATION

CLAIM OF PRIORITY

This application claims the benefit of priority under 35. U.S.C. §119(e) of U.S. Provisional Patent Application Ser. No. 61/897,739, filed on Oct. 30, 2013, which is herein incorporated by reference in its entirety.

FIELD OF THE INVENTION

The present invention relates to tissue stimulation systems, and more particularly, to a system and method for stimulating spinal cord tissue.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems have been applied to restore some functionality to paralyzed extremities in spinal cord injury patients.

Each of these implantable neurostimulation systems typically includes one or more electrode carrying stimulation leads, which are implanted at the desired stimulation site, and a neurostimulator implanted remotely from the stimulation site, but coupled to the stimulation lead(s). Thus, electrical pulses can be delivered from the neurostimulator to the stimulation lead(s) to stimulate or activate a volume of neural tissue. In particular, electrical energy conveyed between at least one cathodic electrode and at least one anodic electrodes creates an electrical field, which when strong enough, depolarizes (or "stimulates") the neurons beyond a threshold level, thereby inducing the firing of action potentials (APs) that propagate along the neural fibers.

Stimulation energy may be delivered to the electrodes during and after the lead placement process in order to verify that the electrodes are stimulating the target neural elements and to formulate the most effective stimulation regimen. The regimen will dictate which of the electrodes are sourcing current pulses (anodes) and which of the electrodes are sinking current pulses (cathodes) at any given time, as well as the magnitude and duration of the current pulses. The stimulation regimen will typically be one that provides stimulation energy to all of the target tissue that must be stimulated in order to provide the therapeutic benefit, yet minimizes the volume of non-target tissue that is stimulated. In the case of SCS, such a therapeutic benefit is "paresthesia," i.e., a tingling sensation that is effected by the electrical stimuli applied through the electrodes.

To produce the feeling of paresthesia without inducing discomfort or involuntary motor movements within the patient, it is often desirable to preferentially stimulate nerve fibers in the dorsal column (DC nerve fibers), which primarily include sensory nerve fibers, over nerve fibers in the dorsal roots (DR nerve fibers), which include both sensory nerve fibers and motor reflex nerve fibers, as well as those involved with proprioception.

While DC nerve fibers are the intended targets in conventional SCS, in fact, the DR nerve fibers often are recruited first because of geometric, electric, anatomical, and physiological reasons. For example, the DR nerve fibers include fibers with larger diameters than the largest nearby DC nerve fibers, and thus, have a lower threshold at which they are excited. Other factors that contribute to the lower threshold of the DR fibers include their potentially preferential orientation over that of the DC fibers, and the inhomogeneity and anisotropy of the surrounding medium at the entrance of the DR nerve fibers into the spinal cord. Thus, DR nerve fibers may still generate APs at extracellular stimulation levels than will nearby DC nerve fibers. As a result, the DC nerve fibers that are desired to be stimulated can have a lower probability of stimulation than do the DR nerve fibers, and thus, the proprioceptive fibers can often be recruited leading to patient discomfort. Also, the motor reflex arc can be activated leading to undesired motor recruitment. Both cases can prevent a paresthesia concordant with the patient's pain area.

For reasons such as these, it is often desirable to preferentially stimulate DC nerve fibers over the DR nerve fibers by modifying the threshold at which neural tissue is activated in a manner that maximizes excitation of the DC nerve fibers, while minimizing excitation of the DR nerve fibers; that is, to increase the DR/DC threshold ratio. This can be accomplished by sinking an electrical pulse to a cathodic electrode located at the center of the spinal cord to depolarize the target tissue adjacent the cathodic electrode, thereby creating APs along the DC nerve fibers, while an electrical pulse can be sourced to anodic electrodes on both sides of the cathodic electrode to hyperpolarize non-target tissue adjacent the anodic electrodes, thereby increasing the threshold of the DR nerve fibers.

In a typical example, in order to stimulate the DC nerve fibers, while guarding against the stimulation of the DR nerve fibers, SCS systems may activate anodes that flank a single cathode in a medial-lateral electrical field, with the single cathode providing the stimulation energy for the DC fibers, while the flanking anodes increase the thresholds, and therefore, guarding against the recruitment, of the DR fibers, as illustrated in FIG. 1.

Because several DR nerve fibers on each side of the spinal cord may be close enough to the cathode to be inadvertently stimulated, several anodes on each side of the cathode may be activated in order to guard against stimulation of these DR nerve fibers. For example, in one approach, a center cathode provides the stimulation energy for the DC fibers, and two pairs of anodes (one pair rostro-caudally flanking the cathode on one transverse side of the spinal cord, and the other pair rostro-caudally flanking the cathode on the other side of the spinal cord) guard against stimulation of the DR nerve fibers, as shown in FIG. 2. Typically, the current is distributed to the anodes equally (i.e., 25% current on each anodes) under the assumption that all loci of dorsal root fibers are equally affected by the anodes.

This assumption may be proper when the DR fibers perpendicularly enter the spinal cord. However, as illustrated in FIG. 3, the angle between the DR nerve fibers and the longitudinal axis of the spinal cord tends to increase as one moves down the spinal cord in the caudal direction (i.e., the DR nerve fibers located at the more rostral vertebral segments will enter the spinal cord at a more shallow angle (perhaps even perpendicularly), whereas the DR nerve fibers located at the more caudal vertebral segments will enter the spinal cord at a steeper angle. In the latter case, an equal current distribution on the anodes illustrated in FIG. 2 may not be optimum.

There, thus, remains a need for an improved technique for preferentially stimulating DC nerve fibers over DR nerve fibers.

SUMMARY OF THE INVENTION

In accordance with a first aspect of the present inventions, a therapeutic neurostimulation system is provided. The neurostimulation system comprises a neurostimulation lead configured for being implanted along a spinal cord of a patient. The neurostimulation lead includes a paddle having a longitudinal axis and an array of electrodes. The electrode array may be arranged in a plurality of columns extending along the longitudinal axis.

The neurostimulation system further comprises a neurostimulation device configured for delivering electrical stimulation energy to actives ones of the electrode array and control/processing circuitry configured for instructing the neurostimulation device to configure an active electrode (e.g., in a first column of electrodes) as a cathode, and two active electrodes (e.g., in a second column of electrodes) longitudinally flanking and laterally offset from the cathode as anodes, selecting a ratio of stimulation amplitude values for the two anodes based on a known longitudinal location of the implanted neurostimulation lead relative to the spinal cord, and instructing the neurostimulation device to distribute the electrical stimulation energy between the two anodes in accordance with the selected stimulation amplitude value ratio.

In an optional embodiment, the control/processing circuitry is further configured for instructing the neurostimulation device to configure two other active electrodes (e.g., in a third column of electrodes) longitudinally flanking and laterally offset from the cathode as anodes, selecting another ratio of stimulation amplitude values for the two other anodes based on the known longitudinal location of the implanted neurostimulation lead relative to the spinal cord, and instructing the neurostimulation device to distribute the electrical stimulation energy between the two other anodes in accordance with the other selected stimulation amplitude value ratio.

The control/processing circuitry is configured for determining the more rostral one of the two anodes and the more caudal one of the two anodes. The stimulation amplitude value for the more rostral anode may be greater than the stimulation amplitude value for the more caudal anode based on the longitudinal location of the neurostimulation lead.

Specifically, the control/processing circuitry is configured for selecting a first ratio of the stimulation amplitude values for the two anodes if the longitudinal location is in a cervical region of the spinal cord, and selecting a second ratio of the stimulation amplitude values if the longitudinal location is in a thoracic region of the spinal cord. The first stimulation amplitude ratio is closer to unity than the second amplitude ratio. In one embodiment, the second stimulation amplitude ratio is at least two. In another embodiment, the second stimulation amplitude ratio is at least four.

The neurostimulation system may further comprise a memory configured for storing a look-up table containing a plurality of different stimulation amplitude ratios and associated neurostimulation lead locations. The control/processing circuitry is configured for selecting the stimulation amplitude ratio by matching the known longitudinal location of the neurostimulation lead relative to the spinal cord with one of the neurostimulation lead locations stored in the look-up table and selecting the stimulation amplitude ratio associated with the matched neurostimulation lead location.

In one embodiment, the control/processing circuitry may be contained within the neurostimulation device. In an alternate embodiment, the control/processing circuitry may be contained in an external controller.

In one embodiment, the neurostimulation device may be configured for determining the known longitudinal location of the implanted neurostimulation lead relative to the spinal cord. In an alternative embodiment, the neurostimulation lead may further comprise a user interface configured for receiving user input defining the known longitudinal location of the implanted neurostimulation lead relative to the spinal cord.

In accordance with a second aspect of the present inventions, an external controller for use with a neurostimulation device coupled to an array of electrodes arranged in along a longitudinal axis (e.g., in columns) of the spinal cord of the patient is provided. The external controller comprises a user interface (e.g., a directional control device) configured for receiving user input (e.g., identifying a desired stimulation area relative to the electrode array), control/processing circuitry configured for generating a set of stimulation parameters in response to the user input, the stimulation parameter set including an electrode combination designating one of the electrodes (e.g., in a first column of electrodes) as a cathode, and two electrodes (e.g., in a second column of electrodes) longitudinally flanking and laterally offset from the cathode as anodes, and output circuitry configured for transmitting the stimulation parameter set to the neurostimulation device. The stimulation parameter set further includes stimulation amplitude values for the two anodes having a ratio based on a known longitudinal location of the implanted neurostimulation lead relative to the spinal cord.

The control/processing circuitry may be further configured for generating a series of sets of stimulation parameters in response to the user input, each of which includes an electrode combination designating one of the electrodes in a first one of the columns as a cathode, and two electrodes longitudinally flanking the cathode in a second one of the columns as anodes.

The control/processing circuitry may select the appropriate ratio of the stimulation amplitudes of the anodes in the same manner described above and designate two other electrodes longitudinally flanking and laterally offset from the cathode as anodes in the same manner described above.

In accordance with a third aspect of the present inventions, a method of providing therapy to a patient using an array of electrodes arranged along a longitudinal axis of the spinal column of the patient (e.g., in a plurality of columns) is disclosed. The method comprises determining a longitudinal location of the electrode array relative to the spinal cord, configuring an electrode (e.g., in a first column of electrodes) as a cathode, and two electrodes longitudinally flanking and laterally offset from the cathode (e.g., in a second column of electrodes) as anodes, selecting a ratio of stimulation amplitude values for the two anodes based on the determined longitudinal location of the implanted neurostimulation lead relative to the spinal cord, and delivering electrical stimulation energy to the active ones of the electrodes, such that the electrical stimulation energy is distributed between the two anodes in accordance with the selected stimulation amplitude value ratio. In an optional method, two more electrodes longitudinally flanking and laterally offset from the cathode (e.g., in a third column of electrodes) may be configured as anodes and electrical energy may be distributed among all the anodes in the same manner described above.

The longitudinal location of the electrode array relative to the spinal cord may be determined automatically or manually in the same manner described above. The method of selecting the ratio of the stimulation amplitudes of the anodes may be performed in the same manner described above.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 9 is a table illustrating a ratio of stimulation amplitudes for anodes on a particular column of the neurostimulation lead based on a longitudinal location of the implanted neurostimulation lead of FIG. 6 with respect to the spinal cord;

DETAILED DESCRIPTION OF THE EMBODIMENTS

Figure 4:
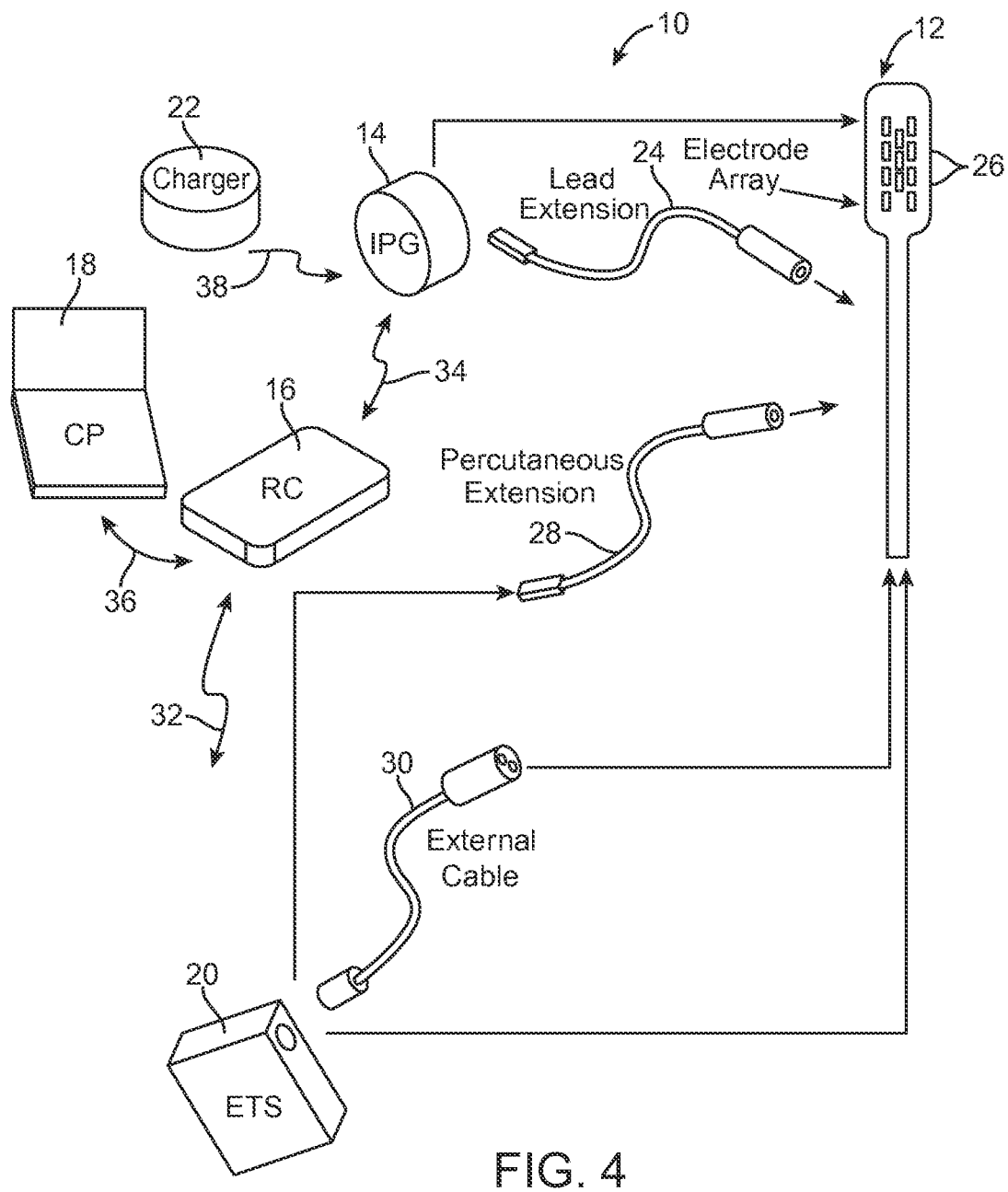
FIG. 4 is a plan view of one embodiment of a spinal cord stimulation (SCS) system arranged in accordance with the present inventions.

Turning first to FIG. 4, an exemplary spinal cord stimulation (SCS) system 10 generally comprises an implantable stimulation lead 12, an implantable pulse generator (IPG) 14 (or alternatively RF receiver-stimulator), an external remote control RC 16, a Clinician's Programmer (CP) 18, an External Trial Stimulator (ETS) 20, and an external charger 22.

The IPG 14 is physically connected via a lead extension 24 to the stimulation lead 12, which carries a plurality of electrodes 26 arranged in an array. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20, which has similar pulse generation circuitry as the IPG 14, also provides electrical stimulation energy to the electrode array 26 in accordance with a set of stimulation parameters. The major difference between the ETS 20 and the IPG 14 is that the ETS 20 is a non-implantable device that is used on a trial basis after the stimulation lead 12 has been implanted and prior to implantation of the IPG 14, to test the effectiveness of the stimulation that is to be provided.

The RC 16 may be used to telemetrically control the ETS 20 via a bi-directional RF communications link 32. Once the IPG 14 and stimulation lead 12 are implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The external charger 22 is a portable device used to transcutaneously charge the IPG 14 via an inductive link 38.

The clinician detailed stimulation parameters provided by the CP 18 are also used to program the RC 16, so that the stimulation parameters can be subsequently modified by operation of the RC 16 in a stand-alone mode (i.e., without the assistance of the CP 18). In the present invention, the CP 18 may be used to determine a longitudinal location of the electrodes 26 in relation to the spinal cord, based on which electrical energy is optimally delivered to the electrodes such that nerve fibers in the dorsal column (DC nerve fibers) are preferentially stimulated over nerve fibers in the dorsal roots (DR nerve fibers), as will be described in further detail below.

For the purposes of this specification, the terms "neurostimulator," "stimulator," "neurostimulation," and "stimulation" generally refer to the delivery of electrical energy that affects the neuronal activity of neural tissue, which may be excitatory or inhibitory; for example by initiating an action potential, inhibiting or blocking the propagation of action potentials, affecting changes in neurotransmitter/neuromodulator release or uptake, and inducing changes in neuroplasticity or neurogenesis of brain tissue. For purposes of brevity, the details of the RC 16, ETS 20, and external charger 22 will not be described herein. Details of exemplary embodiments of these devices are disclosed in U.S. Pat. No. 6,895,280, which is expressly incorporated herein by reference.

Figure 5:
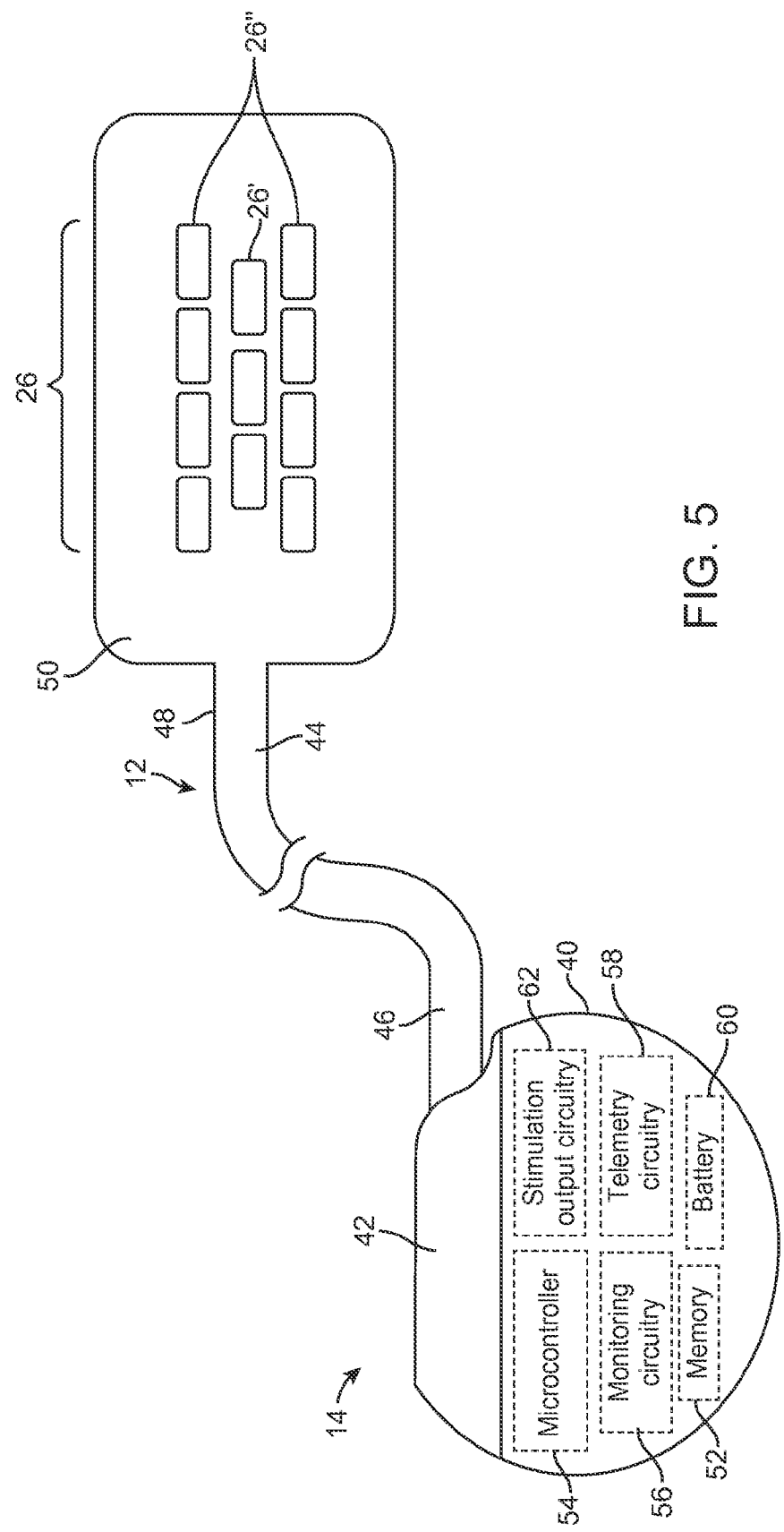
FIG. 5 is a plan view of an implantable pulse generator (IPG) and a paddle neurostimulation lead used in the SCS system of FIG. 4.

Referring now to FIG. 5, the external features of the neurostimulation leads 12 and the internal components of the IPG 14 will be briefly described. The IPG 14 comprises an outer case 40 for housing the electronic and other components (described in further detail below), and a connector 42 in which the proximal end of the stimulation lead 12 mates in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 serves as an electrode.

As best illustrated in FIG. 5, the neurostimulation lead 12 takes the form of a surgical paddle lead that comprises an elongated body 44 having a proximal end 46 and a distal end 48, and a paddle-shaped membrane 50 formed at the distal end 48 of the lead body 44. Further details regarding the construction and method of manufacture of paddle leads are disclosed in U.S. patent application Ser. No. 11/319,291, entitled "Stimulator Leads and Methods for Lead Fabrication," the disclosure of which is expressly incorporated herein by reference.

In the illustrated embodiment, the electrodes 26 are arranged in three columns along the longitudinal axis of the stimulation lead 12. In particular, the electrodes 26 are arranged in one inner column of electrodes 26', and two outer columns of electrodes 26" that flank and are immediately adjacent to the inner electrode column 26'. Each of the electrodes 26 is composed of an electrically conductive, non-corrosive, material, such as, e.g., platinum, titanium, stainless steel, or alloys thereof.

It should be appreciated that in alternative embodiments, the electrodes 26 may be arranged in more than three columns. For example, if four columns are used, there may be two inner electrode columns, and two outer electrode columns flanking the two inner electrode columns. Although the stimulation lead 12 is shown as having eleven electrodes 26, the number of electrodes may be any number suitable for the application in which the stimulation lead 12 is intended to be used (e.g., five, eight, fourteen, etc.). Although the electrode columns of the stimulation paddle lead 12 illustrated in FIG. 5 are shown as having uniform spacing, it should be appreciated that the spacing between the electrode columns may be suitably varied. Further details regarding alternate configurations of the paddle lead are disclosed in U.S. Pat. No. 8,437,857, entitled "Multiple tunable central cathodes on a paddle for increased medial-lateral and rostral-caudal flexibility via current steering," the disclosure of which is expressly incorporated herein by reference.

The IPG 14 comprises electronic components, such as a memory 52, controller/processor (e.g., a microcontroller) 54, monitoring circuitry 56, telemetry circuitry 58, a battery 60, stimulation output circuitry 62, and other suitable components known to those skilled in the art.

The memory 52 is configured for storing programming packages, stimulation parameters, and other important information necessary for proper functioning of the IPG 14. The microcontroller 54 executes a suitable program stored in memory 52 for directing and controlling the neurostimulation performed by IPG 14. The monitoring circuitry 56 is configured for monitoring the status of various nodes or other points throughout the IPG 14, e.g., power supply voltages, temperature, battery voltage, and the like. The telemetry circuitry 58, including an antenna (not shown), is configured for receiving programming data (e.g., the operating program and/or stimulation parameters) from the RC 16 and/or CP 18 in an appropriate modulated carrier signal, which the programming data is then stored in the memory 52. The telemetry circuitry 58 is also configured for transmitting status data to the RC 16 and/or CP 18 in an appropriate modulated carrier signal. The battery 60, which may be a rechargeable lithium-ion or lithium-ion polymer battery, provides operating power to IPG 14. The stimulation output circuitry 62 is configured for, under control of the microcontroller 54, generating and delivering electrical energy, in the form of electrical pulse trains, to each of the electrodes 26.

With respect to the electrical energy delivered by the stimulation output circuitry 62, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case, as mentioned above, so that the electrical current has a path from the energy source contained within the IPG case to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes is activated along with the case of the IPG 14, so that electrical energy is transmitted between the selected electrode and case. Monopolar delivery may also occur when one or more of the lead electrodes are activated along with a large group of lead electrodes located remotely from the one more lead electrodes so as to create a monopolar effect; that is, electrical energy is conveyed from the one or more lead electrodes in a relatively isotropic manner. Multipolar delivery occurs when two or more of the lead electrodes are activated as anode and cathode, so that electrical energy is transmitted between the selected electrodes.

Figure 6:
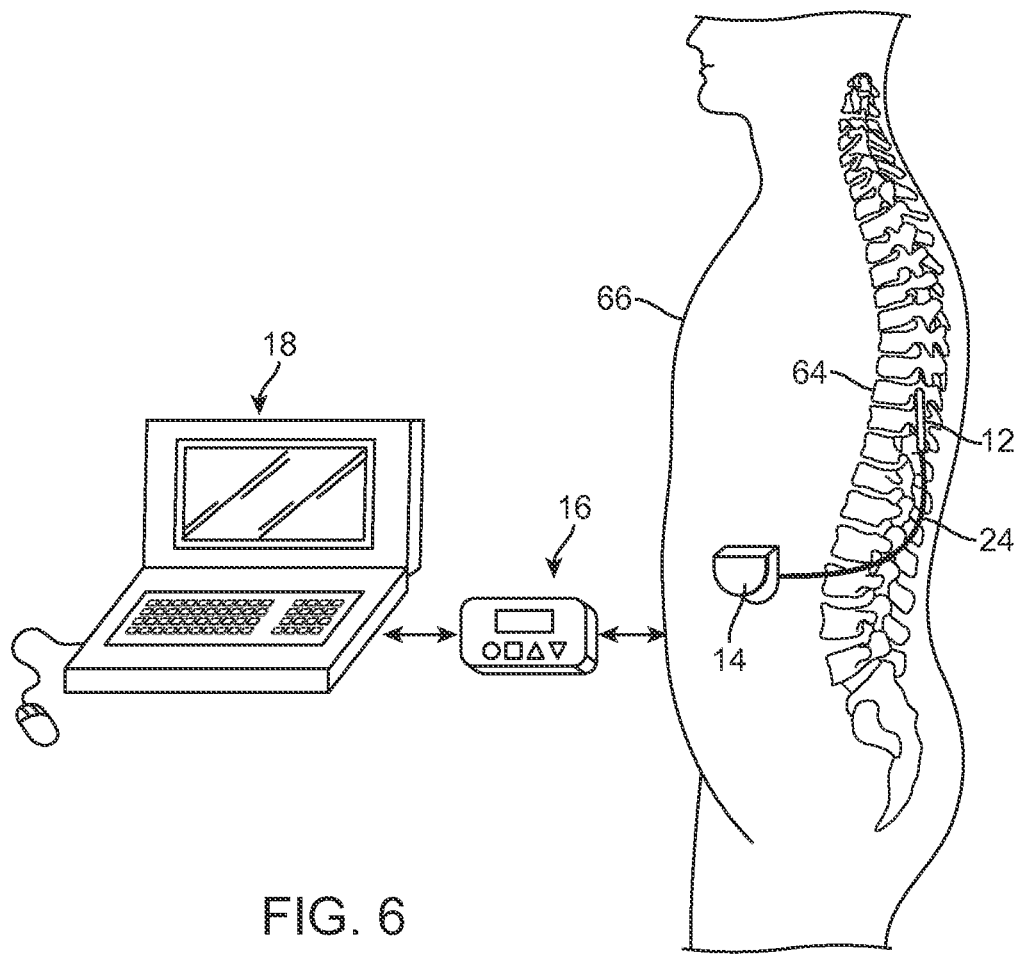
FIG. 6 is a plan view of the SCS system of FIG. 4 in use with a patient.

As shown in FIG. 6, the implantable neurostimulation lead 12 is implanted within the spinal column 64 of a patient 66. The preferred placement of the neurostimulation lead 12 is adjacent, i.e., in the epidural space above the spinal cord area to be stimulated. Due to the lack of space near the location where the neurostimulation lead 12 exits the spinal column 64, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the stimulation lead 12. As there shown, the CP 18 communicates with the IPG 14 via the RC 16.

More significant to the present inventions, to preferentially stimulate the DC nerve fibers over the DR nerve fibers during the course of neurostimulation therapy for the patient, the SCS system 10 is configured for generating an appropriate medial-lateral electric field that is strategically oriented in a manner that avoids stimulating the DR nerve fibers. For the purposes of this specification, a "medial-lateral field" means that the strongest field components are oriented approximately parallel to the medial-lateral axis, as opposed to a "rostral-caudal field," which means that the strongest field components are oriented approximately parallel to the rostral-caudal axis. The medial-lateral electric field is created by a lateral configuration of cathode(s) and anode(s) in the neurostimulation lead 12 and the conveyance of electrical energy between them.

Figure 7:
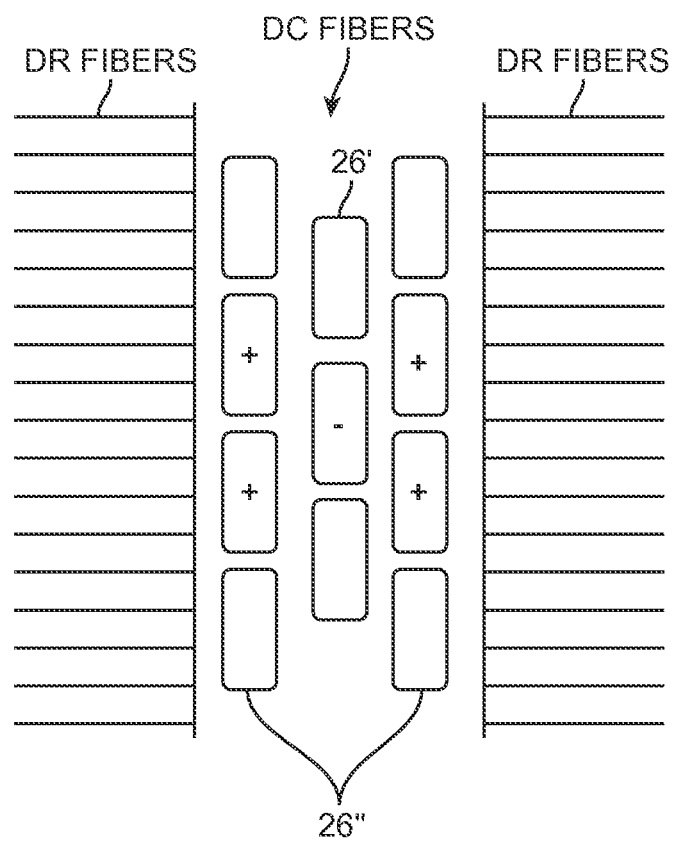
FIG. 7 is a coronal view of a cathode-anode electrode arrangement that can create a medial-lateral electrical field to stimulate spinal cord tissue using the neurostimulation lead of FIG. 5.

To this end, the neurostimulation lead 12 may be implanted within the patient, such that the electrodes 26 are disposed adjacent to the spinal cord, with the middle column of electrodes disposed directly over the DC nerve fibers, and the outer electrode columns disposed directly over the DR nerve fibers, as illustrated in FIG. 7. As can be seen, the middle column of electrodes 26' is maintained away from the DR nerve fibers to prevent the inadvertent stimulation of the DR nerve fibers.

In particular, the IPG 14 may configure at least one of the electrodes in the middle column 26' as a cathode, and at least two of the electrodes in at least one outer electrode columns 26" as anodes, such that electrical stimulation energy conveyed from the IPG 14 between the cathode(s) and anode(s) creates a medial-lateral electrical field that stimulates the DC fibers, while preventing stimulation of the DR fibers. In the electrode arrangement illustrated in FIG. 7, the IPG 14 configures the central electrode of the middle column of electrodes 26' as a cathode, while configuring the two rows of outer electrodes that flank the cathode (i.e., the two immediately adjacent electrodes of the left outer column 26" and two immediately adjacent electrodes of the right outer column 26" that longitudinally flank the cathode in the middle column) as anodes. The exact configuration of the activated electrodes and the electrical energy delivered to them may be modified based on the desired size and locus of the medial-lateral electric field.

More specifically, the size of the medial-lateral electric field is partly based on the spacing between the cathode(s) and anode(s) of the neurostimulation lead 12. A larger spacing between the cathode(s) and the anode(s) will result in a larger medial-lateral electric field, and similarly, a smaller spacing between the cathode(s) and the anode(s) will result in a smaller medial-lateral electric field. For illustrative purposes, the following discussion will focus on the tight spacing between the cathode and the anodes, as shown in FIG. 7, but it should be appreciated that the spacing between the cathode and the anodes may be increased (e.g., the top and bottom pairs of electrodes in the two outer electrode columns 26" may be configured as anodes instead of the middle two pairs of electrodes) to change the size of the medial-lateral electric field and the spacings need not be symmetric among any or all electrodes.

The locus of the medial-lateral electric field is based on a distribution of cathodic current among the activated electrodes. For example, if 100% of the cathodic energy is allocated to a single cathode, as shown in FIG. 7, the locus of the medial-lateral electrical field is at the single cathode. If 50% of cathodic energy is allocated to one cathode and the other 50% of the cathodic energy is allocated to another cathode (e.g., any two immediately adjacent electrodes configured as cathodes in the inner electrode column 26'), the locus of the medial-lateral electric field will be situated in between the two cathodes. It should be appreciated that if the distribution of cathodic energy between the two cathodes is changed such that the first cathode is now allocated more cathodic energy than the other, the locus of the medial-lateral electric field will now be situated closer to the first cathode. For illustrative purposes, the following discussion will focus on one central cathode, as illustrated in FIG. 7, but it should be appreciated that more than one electrode may be configured as cathodes in the inner column 26' to change the locus of the medial-lateral electric field.

It should be appreciated that depending on the targeted area of neurostimulation therapy, the neurostimulation lead 12 may be placed either at the center of the spinal cord, or skewed toward a particular side of the spinal cord. When the neurostimulation lead 12 is skewed to a particular side, only two electrodes on that particular outer electrode column 26" may be configured as anodes (e.g., two middle anodes of the right electrode column 26"flanking the center cathode on the right or two middle anodes of the left electrode column 26"flanking the center cathode on the left) because the generated medial-lateral electric field may be too far away to affect the DR nerve fibers on the other side of the spinal cord. When the neurostimulation lead 12 is placed at the center of the spinal cord, two electrodes each on both outer electrode columns 26" may be configured as anodes (e.g., two middle anodes of the right electrode column 26" and two middle anodes of the left electrode column 26"flanking the center cathode on both sides, as shown in FIG. 7) to guard against stimulation of DR nerve fibers on both sides of the spinal cord. For illustrative purposes, the following discussion will focus on this latter configuration of electrodes having a center cathode and four anodes flanking the center cathode on both sides as shown in FIG. 7. Further details on how the medial-lateral electric field is created and modified are disclosed in U.S. Pat. No. 8,437,857, which has previously been incorporated herein by reference.

The goal of this configuration of electrodes is to ensure that electrical energy originating from the cathode stimulates the DC nerve fibers while the anodes flanking the cathode "push" the electrical energy away from the DR nerve fibers by reducing the depolarization effect contributed by the cathode on the side of the flanking anode(s). Specifically, the anodes longitudinally flanking the cathode on the left side push the electrical energy away from the DR nerve fibers on the left, and similarly, the anodes longitudinally flanking the cathode on the right side push the electrical energy away from the DR nerve fibers on the right.

Figure 1:
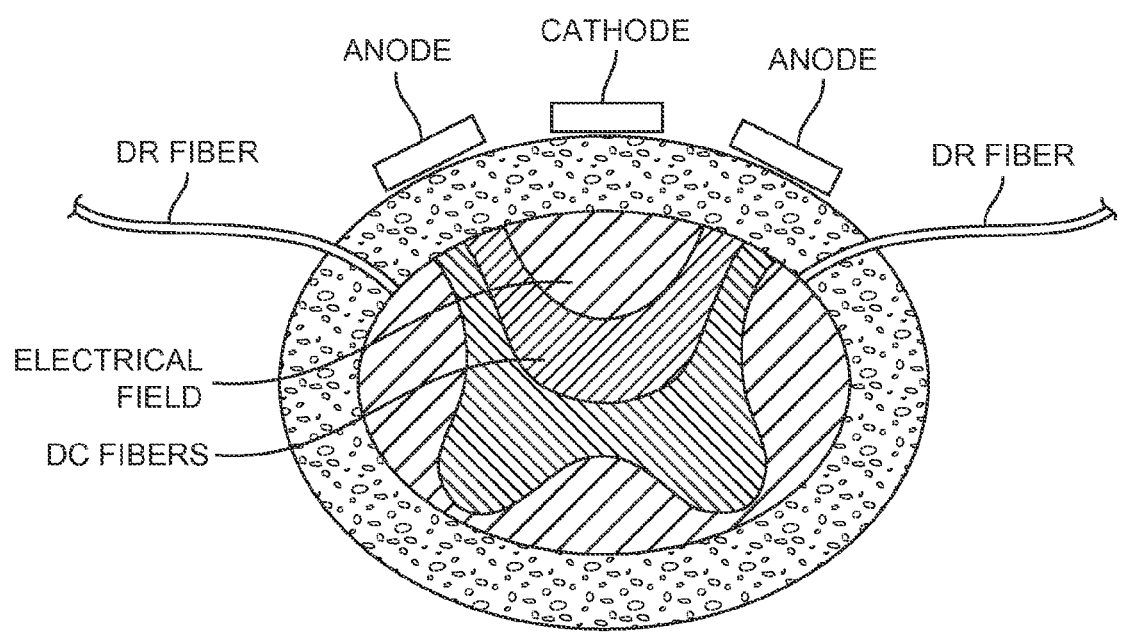
FIG. 1 is a cross-sectional view of a spinal cord and a prior art electrode arrangement for creating a medial-lateral electrical field that stimulates the spinal cord.
Figure 2:
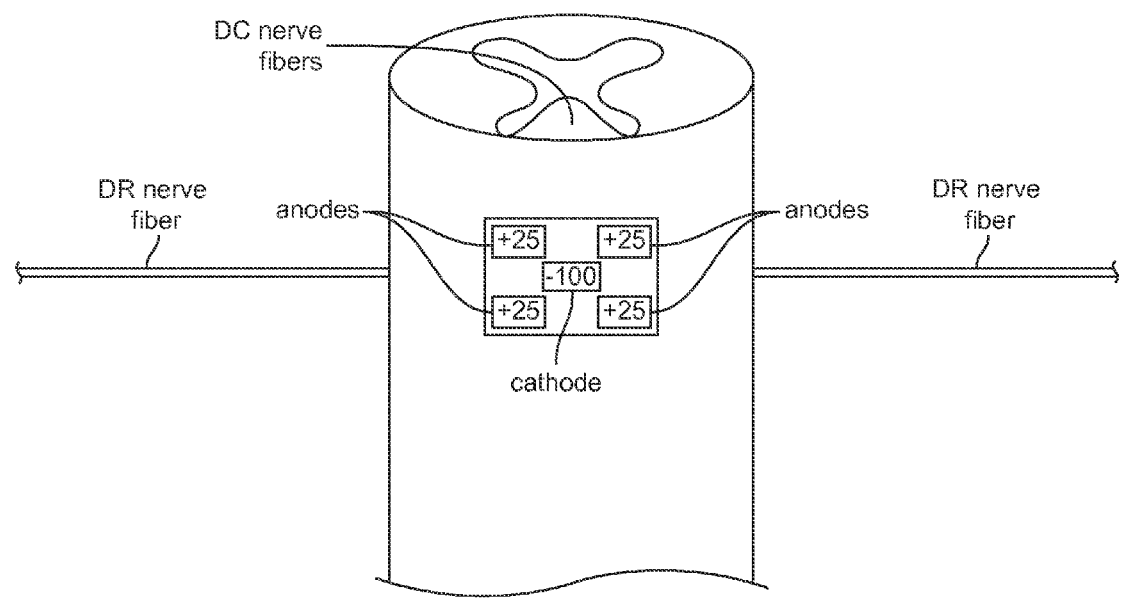
FIG. 2 is a coronal view of the spinal cord and a prior art electrode arrangement for creating a medial-lateral electrical field while avoiding stimulation of dorsal root (DR) nerve fibers.
Figure 3:
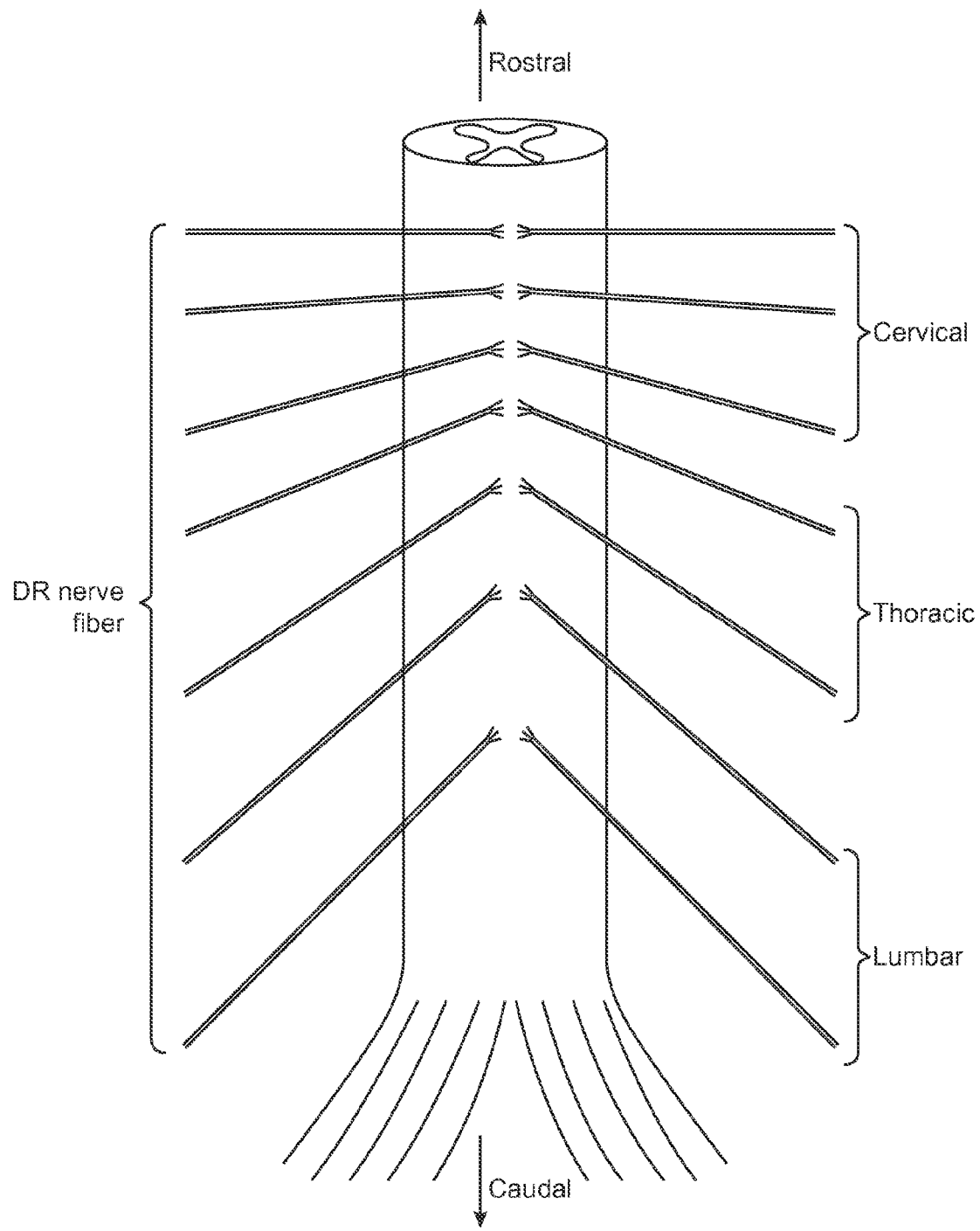
FIG. 3 is a coronal view of the spinal cord depicting the orientation of DR nerve fibers along the spinal cord.

The magnitude of the "push" of electrical energy by a particular anode is directly related to how much anodic current is allocated to that particular anode (i.e., an anode allocated more anodic current will enable a stronger push when compared to an anode allocated less anodic current). For example, if 25% of anodic current is allocated equally to all four anodes as shown in FIG. 7, the rostral anode and caudal anode of a particular electrode column 26"will exhibit an equal push against the electrical energy of the cathode. While this allocation of anodic current works well to prevent stimulation of DR nerve fibers entering the spinal cord almost perpendicularly as shown in FIG. 7, it may not work at a different section of the spinal cord where the angle of the DR nerve fibers entering the spinal cord is steeper (as shown in FIG. 3). Thus, the allocation of anodic current between each pair of longitudinal anodes (anodes on the same column running parallel to the longitudinal DC nerve fibers) should be modified based on the longitudinal location of the neurostimulation lead 12 with respect to the spinal cord (i.e., specific vertebra (e.g., C1-C7, T1-12, etc.) closest to the implanted neurostimulation lead).

To that end, instead of delivering equal amounts of anodic current to both anodes of a particular outer electrode column 26", the distribution of anodic current between each pair of longitudinal anodes is modified in a manner that compensates for the angle of the DR nerve fibers. More specifically, as the angle of the DR nerve fibers entering the spinal cord becomes steeper as one moves in the caudal direction, the ratio of stimulation amplitudes of each longitudinal pair of anodes is increased such that more anodic current is allocated to the more rostral anode as compared to the more caudal anode. It should be appreciated that although the ratio of the stimulation amplitudes of the longitudinal anodes on the right column may be different than that of the left column depending on the area targeted for therapy, it will be assumed in the following discussion that both ratios will be the same, for illustrative purposes.

Figure 8A:
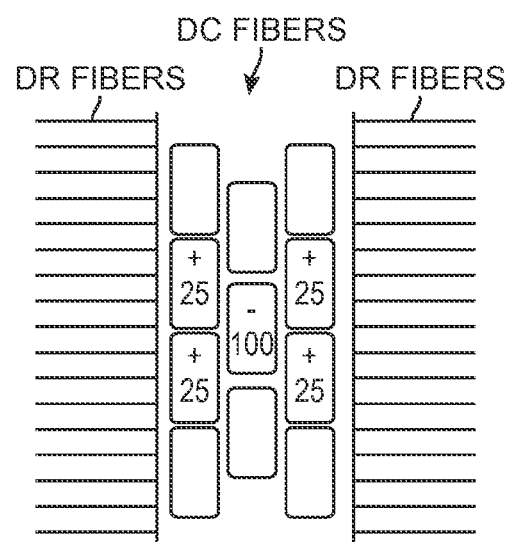
FIG. 8a-8f are coronal views of cathode-anode electrode arrangements created using the neurostimulation lead placed at three different sections of the spinal column.

In particular, as illustrated in FIG. 8a, the IPG 14 is configured for maintaining, between each longitudinal pair of anodes, a low ratio (approaching unity) (e.g., 1:1, i.e., both rostral and caudal anodes are allocated equal anodic current of 25% each) when the DR nerve fibers enter the spinal cord almost perpendicularly (e.g., cervical region of the spinal cord). Such an electrode configuration generates an electrical field having isopotential lines that encircle the cathode in a symmetrical manner, as shown in FIG. 8d. As can be seen, many of the perpendicularly oriented DR nerve fibers between the anodes extend through the electrical field at a relatively oblique angle to the isopotential lines. As a result, the voltage differential along these DR nerve fibers is lessened, thereby decreasing the chance that the DR nerve fibers will be activated.

Figure 8B:
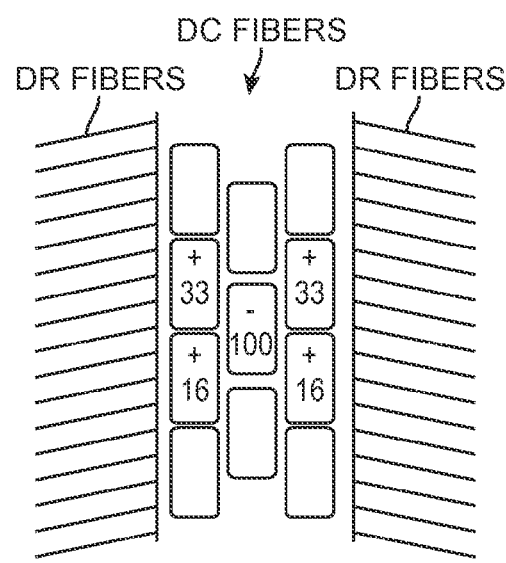

As illustrated in FIG. 8b, the IPG 14 is configured to maintain a moderate ratio (e.g., 2:1, i.e., rostral anode is allocated twice as much anodic current as caudal anode of 33.3% and 16.6% respectively) when the DR nerve fibers enter the spinal cord at a moderately steep angle (e.g., thoracic region of the spinal cord). Such an electrode configuration generates an electrical field having isopotential lines that encircle the cathode in a non-symmetrical manner, with the upper region of the isopotentials being compressed, as shown in FIG. 8e. As can be seen, many of the moderately angled DR nerve fibers between the anodes extend through the electrical field at a relatively oblique angle to the upper region of the isopotential lines. As a result, the voltage differential along these DR nerve fibers is lessened, thereby decreasing the chance that the DR nerve fibers will be activated.

Figure 8C:
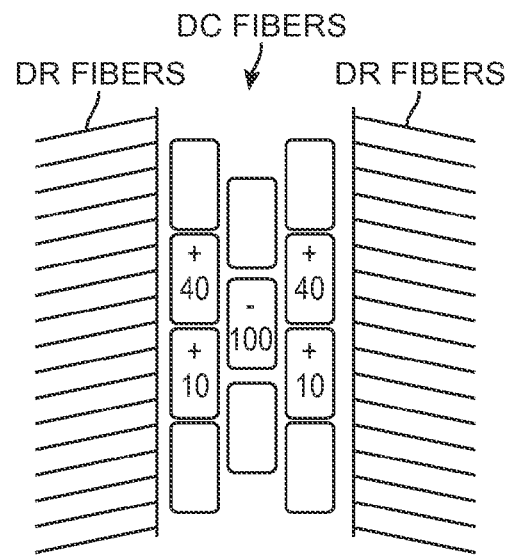
Figure 8D:
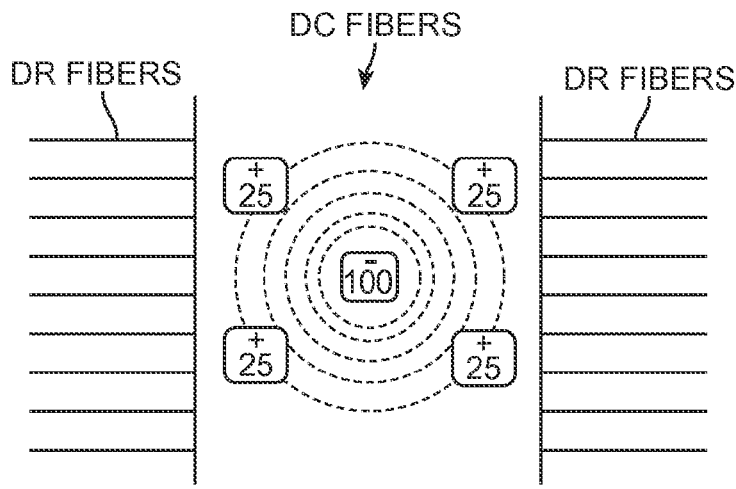
Figure 8E:
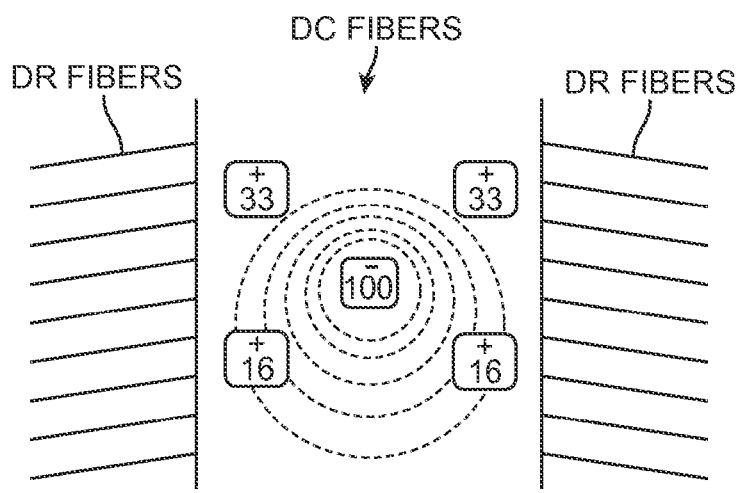
Figure 8F:
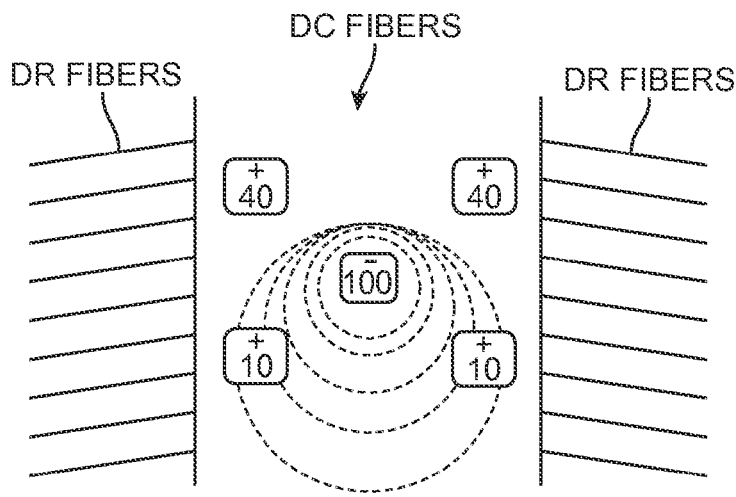

Finally, as illustrated in FIG. 8c, the IPG 14 is configured to maintain a high ratio (e.g., 4:1, i.e., rostral anode is allocated four times as much anodic current as caudal anode of 40% and 10%) when the DR nerve fibers enter the spinal cord at a very steep angle (e.g., lumbar region of the spinal cord). Such an electrode configuration generates an electrical field having isopotential lines that encircle the cathode in a non-symmetrical manner, with the upper region of the isopotentials being even more compressed, as shown in FIG. 8f. As can be seen, many of the steeply angled DR nerve fibers between the anodes extend through the electrical field at a relatively oblique angle to the upper region of the isopotential lines. As a result, the voltage differential along these DR nerve fibers is lessened, thereby decreasing the chance that the DR nerve fibers will be activated.

Based on the above, it is clear that determining the longitudinal location of the neurostimulation lead 12 with respect to the spinal cord is crucial in determining the appropriate ratio of anodic current to be allocated between each pair of longitudinal anodes. In the preferred embodiment, the SCS system 10 is configured for automatically determining the longitudinal location of the implanted neurostimulation lead 12. More specifically, the SCS system 10 may be configured to apply image recognition techniques to a stored medical image (e.g., MRI scan, CT scan, fluoroscopy, etc.) of the patient's spinal cord, and identify the longitudinal location of the implanted neurostimulation lead 12 with respect to the spinal cord.

In an alternate embodiment, the SCS system 10 is configured to aid the user in determining the longitudinal location of the implanted neurostimulation lead. More specifically, the user may view the stored medical image of the patient's spinal cord on the CP 18 and manually input the longitudinal location of the neurostimulation lead through the user interface of the CP 18. More details on this aspect of the invention will be discussed further below.

Once the longitudinal location of the implanted neurostimulation lead 12 has been determined, the SCS system 10 is configured to automatically select the appropriate ratio of stimulation amplitudes of each pair of longitudinal anodes based on the determined longitudinal location of the implanted neurostimulation lead 12.

To this end, the SCS system 10 may refer to a stored look-up table containing a list of different longitudinal locations of the neurostimulation lead 12, each of which corresponds to an appropriate ratio of stimulation amplitudes for the longitudinal pair of anodes to best compensate for the angle of the DR nerve fibers at that particular longitudinal location. Since the angle of the DR nerve fibers typically does not increase drastically at every single vertebra, the look-up table typically contains a list of vertebral levels, each of which encompasses several vertebrae that correspond to the same ratio of stimulation amplitudes.

For example, there may be three vertebral levels: cervical level (C1-C7), thoracic level (T1-T12) and lumbar level (L1-L5). Or, in another example, to account for more subtle differences in the angle of the DR nerve fibers entering the spinal cord, there might be six vertebral levels instead of three: cervical level 1 (C1-C3), cervical level 2 (C4-C7), thoracic level 1 (T1-T6), thoracic level 2 (T7-T12), lumbar level 1 (L1-L2) and lumbar level 2 (L3-L4). In yet another example, to be even more precise, every vertebra of the vertebral column might constitute its own vertebral level (C1 level, C2 level, C3 level, etc.). Alternatively, rather than storing the ratios in a look-up table, they can be dynamically determined based on a mathematical formulation.

Referring now to FIG. 9, one exemplary embodiment of selecting the ratio of stimulation amplitudes of the anodes based on the longitudinal location of the implanted neurostimulation lead 12 is illustrated. If the determined longitudinal location of the implanted neurostimulation lead 12 is the cervical region of the vertebral column (C1-C7), the ratio between the rostral anode and the caudal anode of each column of anodes flanking the central cathode is automatically configured to be 1:1. If the determined longitudinal location of the implanted neurostimulation lead 12 is the thoracic region of the vertebral column (T1-T12), the ratio between the rostral anode and the caudal anode of each column of anodes flanking the central cathode is automatically configured to be 2:1. Similarly, if the determined longitudinal location of the implanted neurostimulation lead 12 is the lumbar region of the vertebral column (L1-L5), the ratio between the rostral anode and the caudal anode of each column of anodes flanking the central cathode is automatically configured to be 4:1.

In practice, the above-detailed automatic selection of ratios of stimulation amplitudes for longitudinal pair or electrodes aids the user while programming the stimulation parameters for activated electrodes using the CP 18. It should be appreciated that the user may modify this automatic selection of stimulation amplitudes using the CP 18, as will be described in further detail below.

As shown in FIG. 6, the overall appearance of the CP 18 is that of a laptop personal computer (PC), and in fact, may be implemented using a PC that has been appropriately configured to include a directional-programming device and programmed to perform the functions described herein. Alternatively, the CP 18 may take the form of a mini-computer, personal digital assistant (PDA), etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback and for subsequently programming the IPG 14 with the optimum stimulation parameter. It should be appreciated that although the stimulation amplitudes of the electrodes may be automatically selected, the user may manually override the selected values, as will be described in further detail below.

To allow the user to perform these functions, the CP 18 includes a user input device (e.g., a mouse 76 and a keyboard 78), and a programming display screen 80 housed in a case 82. It is to be understood that in addition to, or in lieu of, the mouse 76, other directional programming devices may be used, such as a trackball, touchpad, joystick, or directional keys included as part of the keys associated with the keyboard 78.

In the illustrated embodiment described below, the display screen 80 takes the form of a conventional screen, in which case, a virtual pointing device, such as a cursor controlled by a mouse, joy stick, trackball, etc., can be used to manipulate graphical objects on the display screen 80. In alternative embodiments, the display screen 80 takes the form of a digitizer touch screen, which may either passive or active. Further details discussing the use of a digitizer screen for programming are set forth in U.S. Provisional Patent Application Ser. No. 61/561,760, entitled "Technique for Linking Electrodes Together during Programming of Neurostimulation System," which is expressly incorporated herein by reference.

Figure 10:
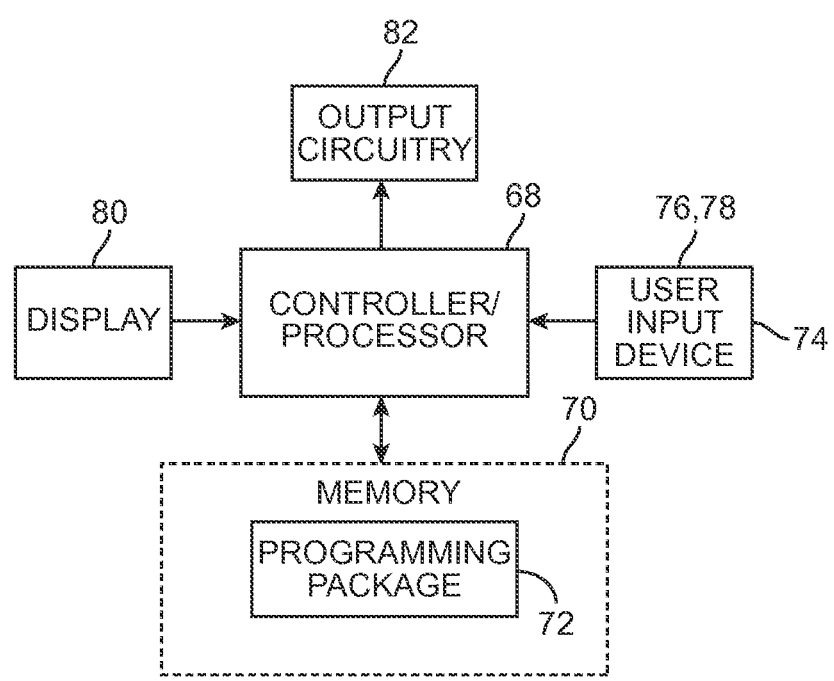
FIG. 10 is a block diagram of a clinician's programmer (CP) used in the SCS system of FIG. 4.

Referring now to FIG. 10, the CP 18 includes a controller/processor 68 (e.g., a central processor unit (CPU)) and memory 70 that stores a programming package 72, which can be executed by the controller/processor 68 to allow the user to program the IPG 14 and RC 16 and a look-up table to be used in selecting a ratio of stimulation amplitudes for each longitudinal pair of anodes based on a longitudinal location of the neurostimulation lead 12. Significant to the present inventions, the controller/processor 68 is configured for selecting the ratio of stimulation amplitudes for each longitudinal pair of anodes based on the determined longitudinal location of the implanted neurostimulation lead 12, and distributing electrical energy between the anodes based on the selected ratio for each longitudinal pair of anodes.

In addition, the CP 18 further includes a user input device 74 (such as the mouse 76 or the keyboard 78 described above) to provide user commands. Notably, while the controller/processor 68 is shown in FIG. 10 as a single device, the processing functions and controlling functions can be performed by a separate controller and processor. Thus, it can be appreciated that the controlling functions described below as being performed by the CP 18 can be performed by a controller, and the processing functions described below as being performed by the CP 18 can be performed by the microcontroller 54 of the IPG 14 or the processor of the RC 16.

Execution of the programming package 72 by the controller/processor 68 provides a multitude of display screens (not shown) that can be navigated through via use of the mouse 76. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), define the configuration and orientation of the leads, initiate and control the electrical stimulation energy output by the neurostimulation leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Modulation energy Among Multiple Neuromodulation Electrodes," which are expressly incorporated herein by reference. Execution of the programming package 72 provides a user interface that conveniently allows a user to program the IPG 14.

Figure 11:
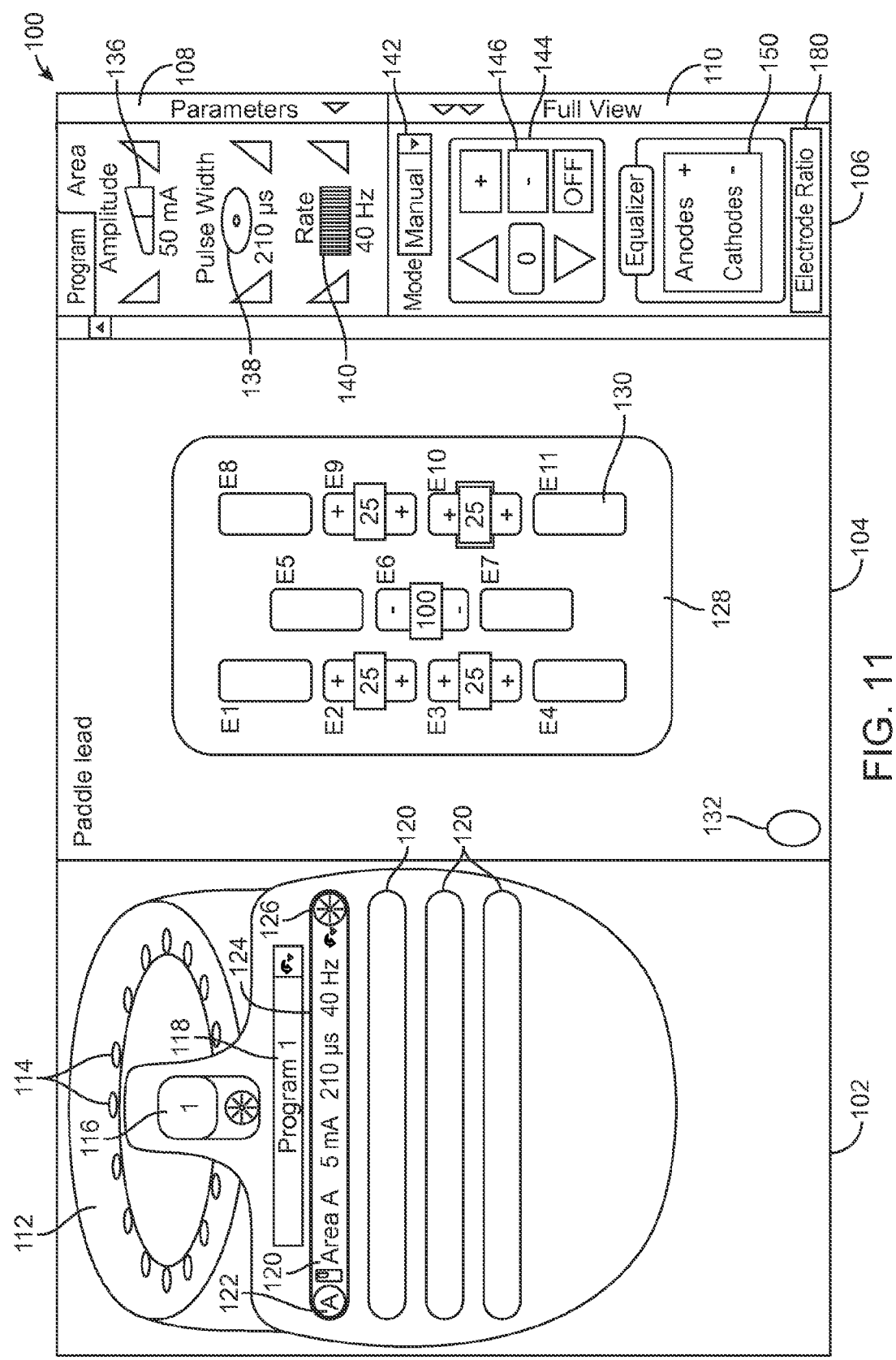
FIG. 11 is a plan view of a user interface of the CP of FIG. 10 in a manual programming mode, wherein the user manually selects the electrodes and allocates electrical energy among them.

Referring now to FIG. 11, a programming screen 100 that can be generated by the CP 18 to allow a user to program the IPG 14 will be described. In the illustrated embodiment, the programming screen 100 comprises three panels: a program selection panel 102, a lead display panel 104, and a stimulation parameter adjustment panel 106. Some embodiments of the programming screen 100 may allow for closing and expanding one or both of the lead display panel 102 and the parameter adjustment panel 106 by clicking on the tab 108 (to show or hide the parameter adjustment panel 106) or the tab 110 (to show or hide the full view of both the lead selection panel 104 and the parameter adjustment panel 106).

The program selection panel 102 provides information about stimulation programs and coverage areas that have been, or may be, defined for the IPG 14. In particular, the program selection panel 102 includes a carousel 112 on which a plurality of stimulation programs 114 (in this case, up to sixteen) may be displayed and selected. The program selection panel 102 further includes a selected program status field 116 indicating the number of the stimulation program 114 that is currently selected (any number from "1" to "16"). In the illustrated embodiment, program 1 is the only one currently selected, as indicated by the number "1" in the field 116. The program selection panel 102 further comprises a name field 118 in which a user may associate a unique name to the currently selected stimulation program 114.

The program selection panel 102 further comprises a plurality of coverage areas 120 (in this case, up to four) with which a plurality of stimulation parameter sets can respectively be associated to create the currently selected stimulation program 114 (in this case, program 1). Each coverage area 120 that has been defined includes a designation field 122 (one of letters "A"-"D"), and an electrical pulse parameter field 124 displaying the electrical pulse parameters, and specifically, the pulse amplitude, pulse width, and pulse rate, of the stimulation parameter set associated with the that coverage area. In this example, only coverage area A is defined for program 1, as indicated by the "A" in the designation field 122. The electrical pulse parameter field 124 indicates that a pulse amplitude of 5 mA, a pulse width of 210 μs, and a pulse rate of 40 Hz has been associated with coverage area A.

Each of the defined coverage areas 120 also includes a selection icon 126 that can be alternately actuated to activate or deactivate the respective coverage area 120. When a coverage area is activated, an electrical pulse train is delivered from the IPG 14 to the electrode array 26 in accordance with the stimulation parameter set associated with that coverage area. Notably, multiple ones of the coverage areas 120 can be simultaneously activated by actuating the selection icons 126 for the respective coverage areas. In this case, multiple electrical pulse trains are concurrently delivered from the IPG 14 to the electrode array 26 during timing channels in an interleaved fashion in accordance with the respective stimulation parameter sets associated with the coverage areas 120. Thus, each coverage area 120 corresponds to a timing channel.

To the extent that any of the coverage areas 120 have not been defined (in this case, three have not been defined), they include text "click to add another program area"), indicating that any of these remaining coverage areas 120 can be selected for association with a stimulation parameter set. Once selected, the coverage area 120 will be populated with the designation field 122, electrical pulse parameter field 124, and selection icon 126.

The lead display panel 104 includes a graphical paddle lead 128, which is illustrated with eleven graphical electrodes 130 each (labeled electrodes E1-E11). The lead display panel 104 also includes a graphical case 132 representing the case 40 of the IPG 14.

The parameter adjustment panel 106 also includes a pulse amplitude adjustment control 136 (expressed in milliamperes (mA)), a pulse width adjustment control 138 (expressed in microseconds (μs)), and a pulse rate adjustment control 140 (expressed in Hertz (Hz)), which are displayed and actuatable in all the programming modes. Each of the controls 136-140 includes a first arrow that can be actuated to decrease the value of the respective stimulation parameter and a second arrow that can be actuated to increase the value of the respective stimulation parameter. Each of the controls 136-140 also includes a display area for displaying the currently selected parameter. In response to the adjustment of any of electrical pulse parameters via manipulation of the graphical controls in the parameter adjustment panel 106, the controller/processor 68 generates a corresponding stimulation parameter set (with a new pulse amplitude, new pulse width, or new pulse rate) and transmits it to the IPG 14 via the telemetry circuitry 58 for use in delivering the stimulation energy to the electrodes 26.

The parameter adjustment panel 106 includes a pull-down programming mode field 142 that allows the user to switch between a manual programming mode, an electronic trolling programming mode, and a navigation programming mode. Each of these programming modes allows a user to define a stimulation parameter set for the currently selected coverage area 120 of the currently selected program 114 via manipulation of graphical controls in the parameter adjustment panel 106 described above, as well as the various graphical controls described below.

The manual programming mode is designed to allow the user to manually define the fractionalized electrical current for the electrode array with maximum flexibility; the electronic trolling programming mode is designed to quickly sweep the electrode array using a limited number of electrode configurations to gradually steer an electrical field relative to the stimulation leads until the targeted stimulation site is located; and the navigation programming mode is designed to sweep the electrode array using a wide number of electrode configurations to shape the electrical field, thereby fine tuning and optimization the stimulation coverage for patient comfort.

As shown in FIG. 11, the manual programming mode has been selected. In the manual programming mode, each of the electrodes 130 of the graphical leads 128, as well as the graphical case 132, may be individually selected, allowing the clinician to set the polarity (cathode or anode) and the magnitude of the current (percentage) allocated to that electrode 130, 132 using graphical controls located in an amplitude/polarity area 144 of the parameter adjustment panel 106.

In particular, a graphical polarity control 146 located in the amplitude/polarity area 144 includes a "+" icon, a "−" icon, and an "OFF" icon, which can be respectively actuated to toggle the selected electrode 130, 132 between a positive polarization (anode), a negative polarization (cathode), and an off-state. An amplitude control 148 in the amplitude/polarity area 144 includes an arrow that can be actuated to decrease the magnitude of the fractionalized current of the selected electrode 130, 132, and an arrow that can be actuated to increase the magnitude of the fractionalized current of the selected electrode 130, 132. The amplitude control 148 also includes a display area that indicates the adjusted magnitude of the fractionalized current for the selected electrode 134. The amplitude control 148 is preferably disabled if no electrode is visible and selected in the lead display panel 104. In response to the adjustment of fractionalized electrode combination via manipulation of the graphical controls in the amplitude/polarity area 144, the controller/processor 68 generates a corresponding stimulation parameter set (with a new fractionalized electrode combination) and transmits it to the IPG 14 via the telemetry circuitry for use in delivering the stimulation energy to the electrodes 26.

In the illustrated embodiment, electrode E6 has been selected as a cathode to which 100% of the cathodic current has been allocated, and electrodes E2, E3, E9 and E10 have been respectively selected as anodes each of which is allocated 25% of the anodic current. Electrode E10 is shown as being selected to allow the user to subsequently allocate the polarity and fractionalized electrical current to it via the graphical controls located in the amplitude/polarity area 144. Although the graphical controls located in the amplitude/polarity area 144 can be manipulated for any of the electrodes, a dedicated graphical control for selecting the polarity and fractionalized current value can be associated with each of the electrodes, as described in U.S. Patent Publication No. 2012/0290041, entitled "Neurostimulation System with On-Effector Programmer Control," which is expressly incorporated herein by reference. In one particular embodiment, the user may select any spot (e.g., by clicking or touching the spot) within the graphical electrodes 130 (including between the electrodes 130), and the controller 68 can generate an ideal multipole relative to the electrodes 130, and determine an electrode combination that emulates the ideal multipole. In this case, the cathode of the virtual multipole will be located at the spot that has been touched or clicked. The virtual multipole in this case will be an ideal longitudinal tripole having a center cathode and a pair of anodes longitudinally disposed on opposite sides of the center cathode. Further details discussing the use of virtual multipoles are described in U.S. Provisional patent application Ser. No. 13/717,298, entitled "Computationally Efficient Technique for Determining Electrode Current Distribution from a Virtual Multipole," which is expressly incorporated herein by reference.

The parameter adjustment panel 106, when the manual programming mode is selected, also includes an equalization control 150 that can be actuated to automatically equalize current allocation to all electrodes of a polarity selected by respective "Anode +" and "Cathode –" icons.

Significant to the present inventions, the parameter adjustment panel 106 comprises an anodic ratio selection control 180 that can be actuated to automatically determine the allocation of anodic current between the anodes flanking the center cathode. In the illustrated embodiment, the user may manually select the cathode and anodes designated for neurostimulation therapy prior to actuating the anodic ratio selection control 180. In an alternate embodiment, the user may simply select the cathode(s), and have the CP 18 determine the configuration of anodes around the selected cathode(s) and the distribution of anodic current between them.

When the anodic ratio selection control 180 is actuated, the controller 68, in consultation with the look-up table, automatically selects the appropriate ratio of stimulation amplitudes of each longitudinal pair of anodes based on the longitudinal location of the neurostimulation lead 12. As mentioned previously, it should be appreciated that the longitudinal location of the neurostimulation lead 12 is determined either automatically or manually and inputted into the CP 18 prior to the programming steps described here.

Figure 12:
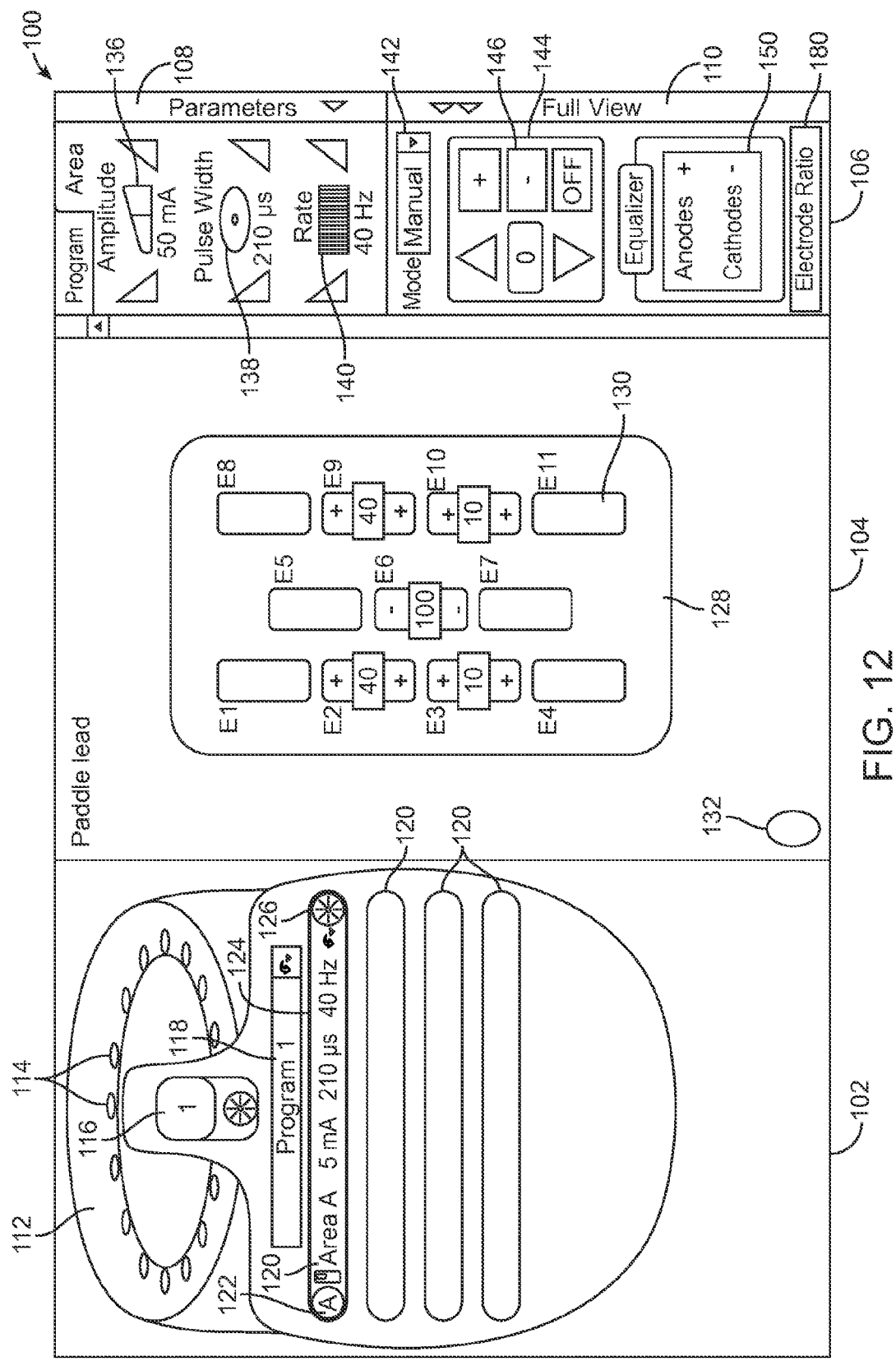
FIG. 12 is a plan view of the user interface in the manual programming mode of FIG. 11, wherein the distribution of electrical energy between the selected electrodes is automatically determined.

For example, as shown in FIG. 12, supposing the longitudinal location of the neurostimulation lead 12 is in the lumbar region (L1-L5), the appropriate ratio of stimulation amplitudes between each longitudinal pair of anodes will be 4:1 (as per the exemplary look-up table illustrated in FIG. 9), based on which the appropriate distribution of anodic current between the electrodes is automatically populated in the lead display 104 (40% of anodic current to each rostral anode and 10% of anodic current to each caudal anode).

Alternatively, rather than having an anodic ratio selection control 180, a spot in the graphical electrodes may be selected (e.g., by clicking or touching it), in which case, the controller 68 will generate an ideal multipole relative to the electrodes 130, and determine an electrode combination that emulates the ideal multipole, as briefly discussed above. The controller 68 will select the appropriate ratio of stimulation amplitudes of each longitudinal pair of anodes based on the longitudinal location of the cathode of the ideal multipole.

Figure 13:
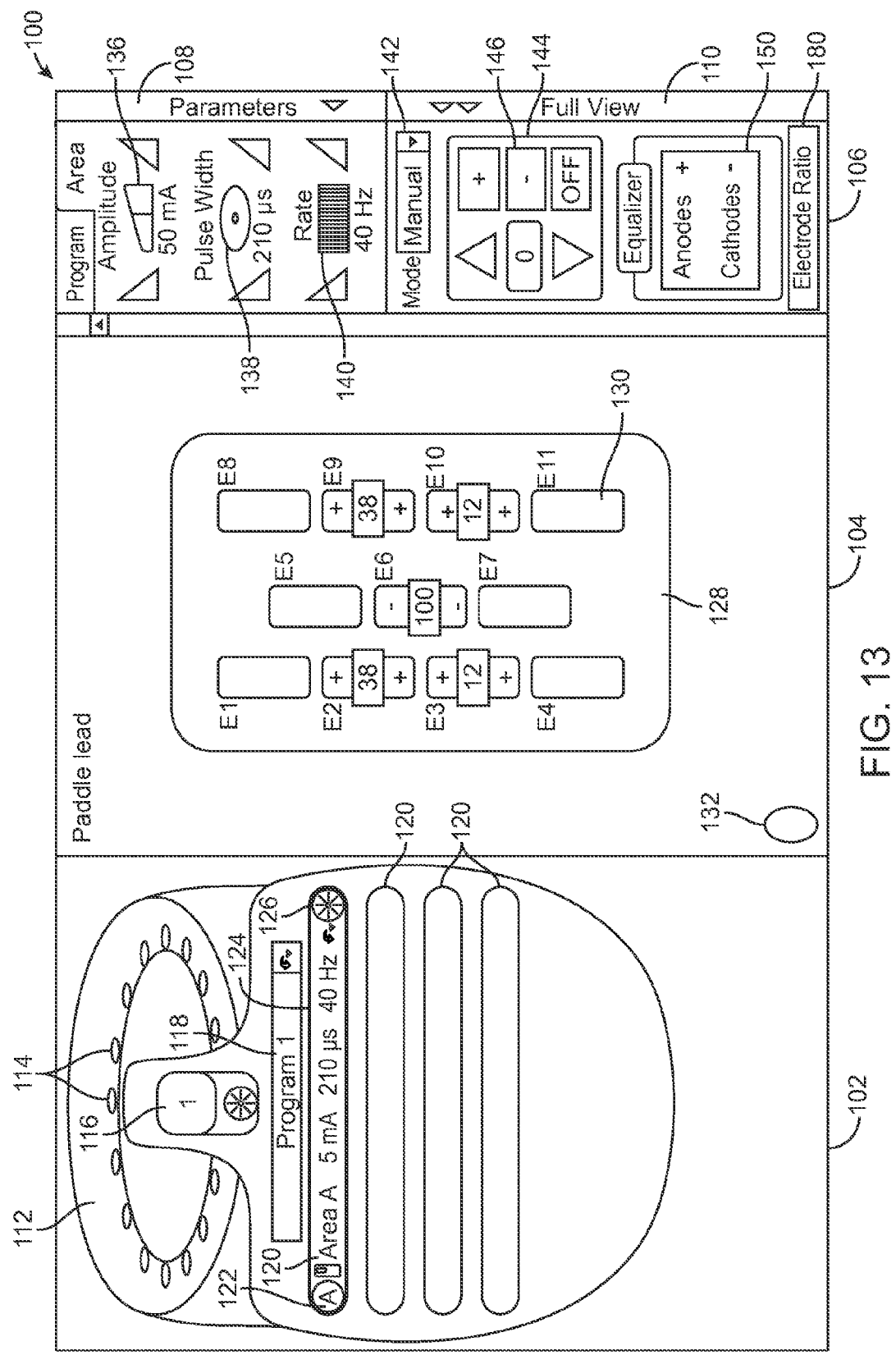
FIG. 13 is a plan view of the user interface in the manual programming mode of FIG. 12, wherein the user manually modifies the automatic distribution of electrical energy between the selected electrodes.

It should be appreciated that the user may manually alter the distribution of current by using the amplitude control 148 to increase or decrease the magnitude and/or fraction of energy delivered to the activated electrodes. For example, as shown in FIG. 13, keeping the suggested distribution of anodic current in mind, the user may slightly alter the distribution using the amplitude control 148 (38% of anodic current to each rostral anode and 12% of anodic current to each caudal anode).

It should be appreciated that if the longitudinal location of the neurostimulation lead 12 falls between two vertebral levels of the look-up table, the distribution of anodic current around one cathode may be different than the distribution of anodic current around another cathode right below it. In other words, the longitudinal location of the desired cathode in relation to the spinal cord may determine the allocation of anodic current around it. For example (not illustrated), supposing the longitudinal location of the neurostimulation lead 12 is such that electrode E5 falls in the thoracic region (T1-T12), but electrodes E6 and E7 fall in the lumbar region (L1-L5), the appropriate ratio of stimulation amplitudes between each pair of longitudinal anodes will be 2:1 if electrode E5 is manually selected, and 4:1 if either electrode E6 or E7 is manually selected. Thus, depending on the longitudinal location of the neurostimulation lead 12 and the granularity of the look-up table, the distribution of anodic current around adjacent cathodes of the middle electrode column 26' may be different. Ostensibly, this scenario is more likely to happen when the look-up table is highly precise (e.g., every vertebra constitutes a separate vertebral level having a different ratio between each pair of longitudinal anodes).

It should be appreciated that the electronic trolling mode may also be used to automatically determine the ratio of stimulation amplitudes of the anodes based on the longitudinal location of the implanted neurostimulation lead 12.

Figure 14:
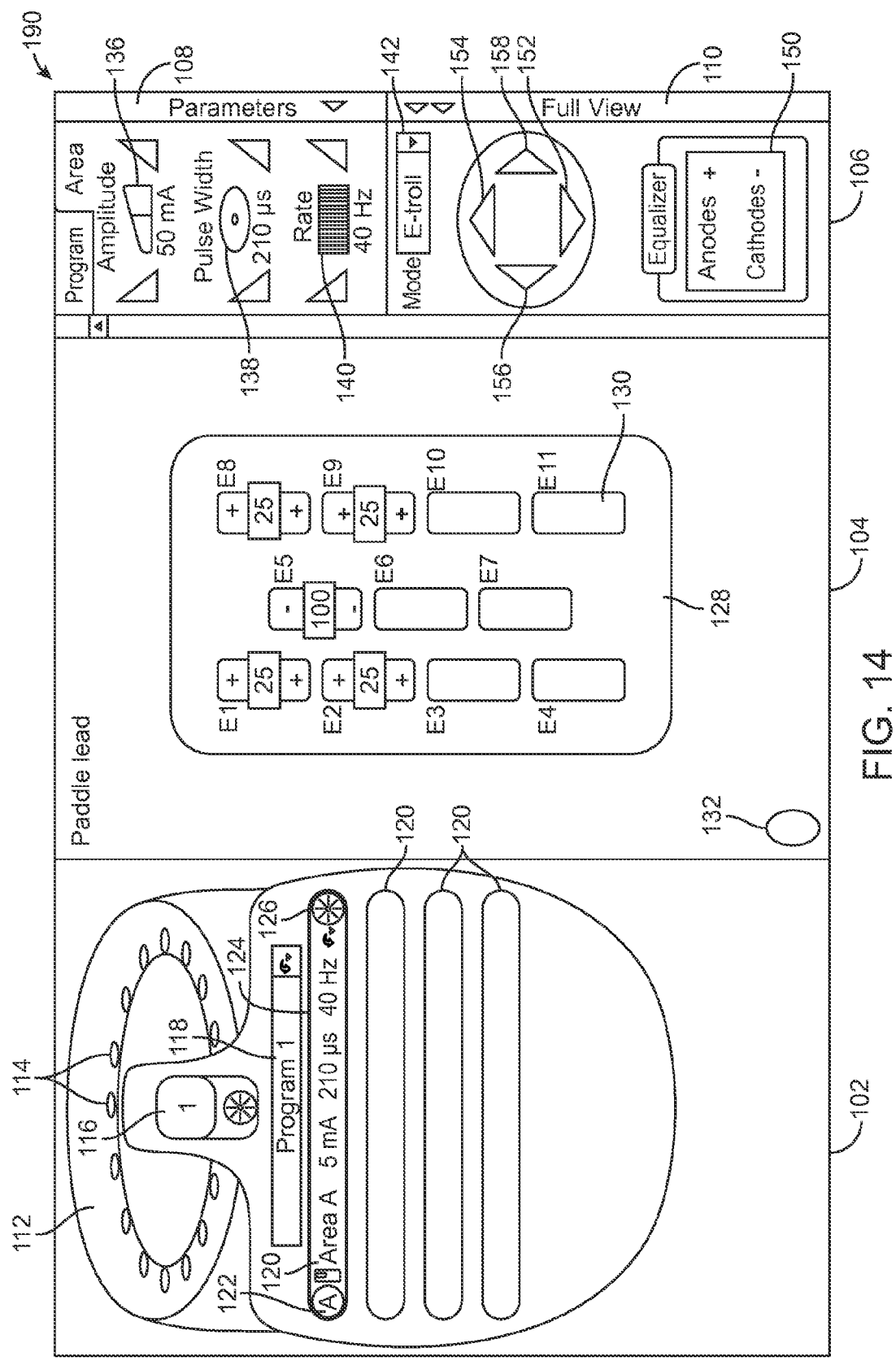
FIG. 14 is a plan view of a user interface of the CP of FIG. 10 in an electronic trolling mode, particularly showing a first fractionalized electrode configuration.

As shown in FIG. 14, the electronic trolling programming mode has been selected. In the electronic trolling mode, the electrodes 130 illustrated in the lead display panel 104 that were individually selectable and configurable in manual programming mode are used for display only and are not directly selectable or controllable. Instead of an amplitude/polarity area 144, the parameter selection panel 106 includes a steering array of arrows 152-158 that allows steering the electrical field up, down, left, or right relative to the electrodes 26.

The electronic trolling mode is a quick way to sweep the electrode array by gradually moving a cathode. Significant to the present inventions, when moving the cathode down the electrode array, the configuration of anodes around the cathode and the distribution of anodic current among them may also change based on the longitudinal location of the cathode, as explained previously. It should be appreciated that in the electronic trolling mode, unlike the case in the manual programming mode, the number of activated electrodes is predetermined. Alternatively, a virtual multipole can be translated relative to the electrode array, and an electrode combination that emulates the ideal multipole can be determined in the same manner briefly discussed above.

Figure 15:
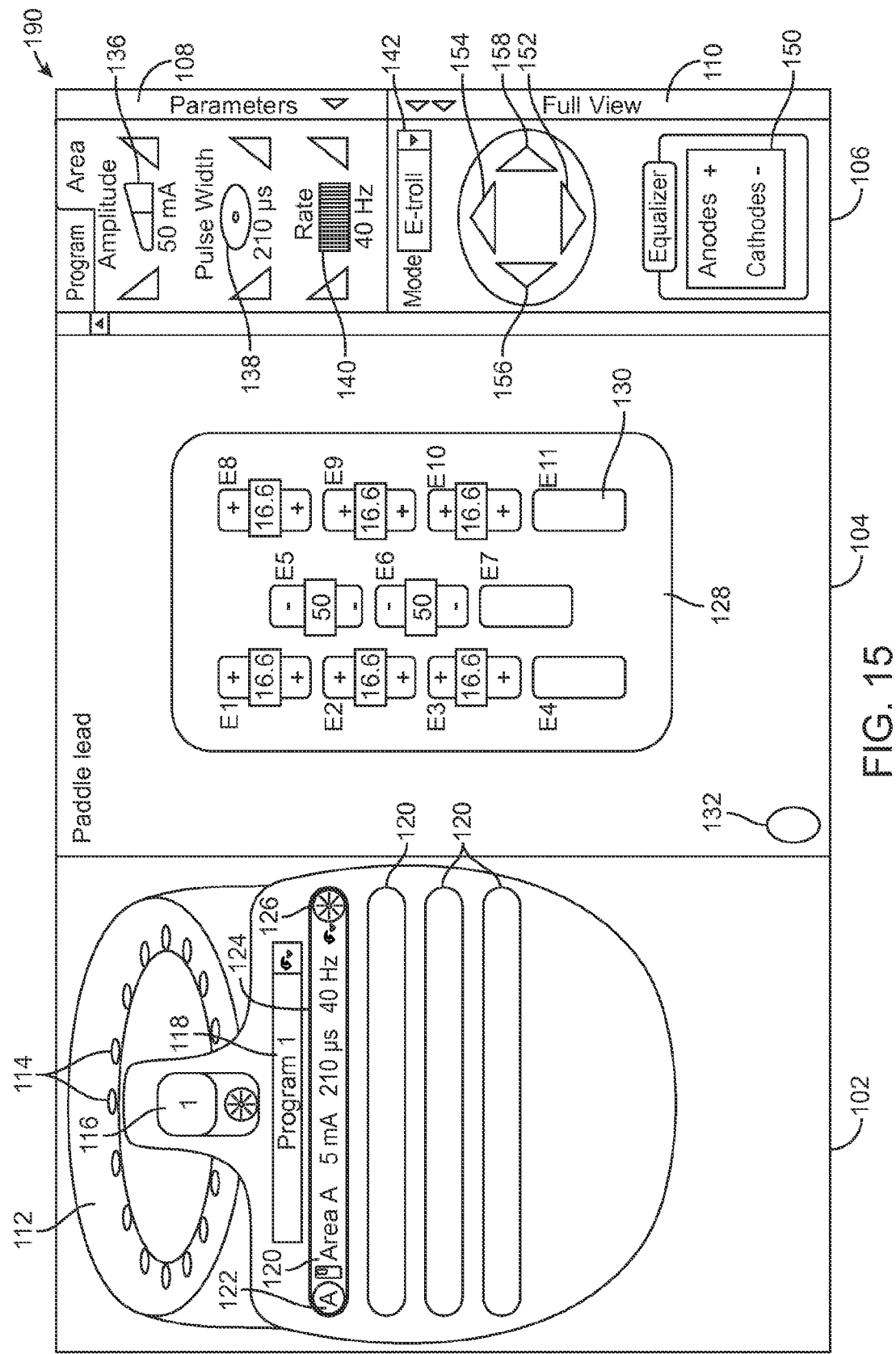
FIG. 15 is a plan view of the user interface in the electronic trolling mode of FIG. 14, particularly showing a second fractionalized electrode configuration.

For example, as shown in FIG. 14, supposing the neurostimulation lead 12 is implanted in the cervical region of the neurostimulation lead 12, the electronic trolling process may begin by designating electrode E5 as the sole cathode and electrodes E1, E2, E8 and E9 as the anodes. As there shown, electrode E5 has a fractionalized cathodic current value of 100%, and electrodes E1, E2, E8 and E9 each have a fractionalized anodic current value of 25%. If the down button 152 is clicked, the cathodic current is gradually shifted from electrode E5 to electrode E6, and the anodic current is gradually shifted down, which gradual shifting occurs in 10% increments. For example, as shown in FIG. 15, the electrical current is shifted, such that electrode E5 has a fractionalized cathodic current value of 50% and electrode E6 has a fractionalized cathodic current value of 50%. Similarly, the anodic current is also shifted down, such that electrodes E3 and E10 are also activated, with the anodic current now being distributed equally over all six anodes, each of which has a fractionalized anodic current value of 16.6%.

Figure 16:
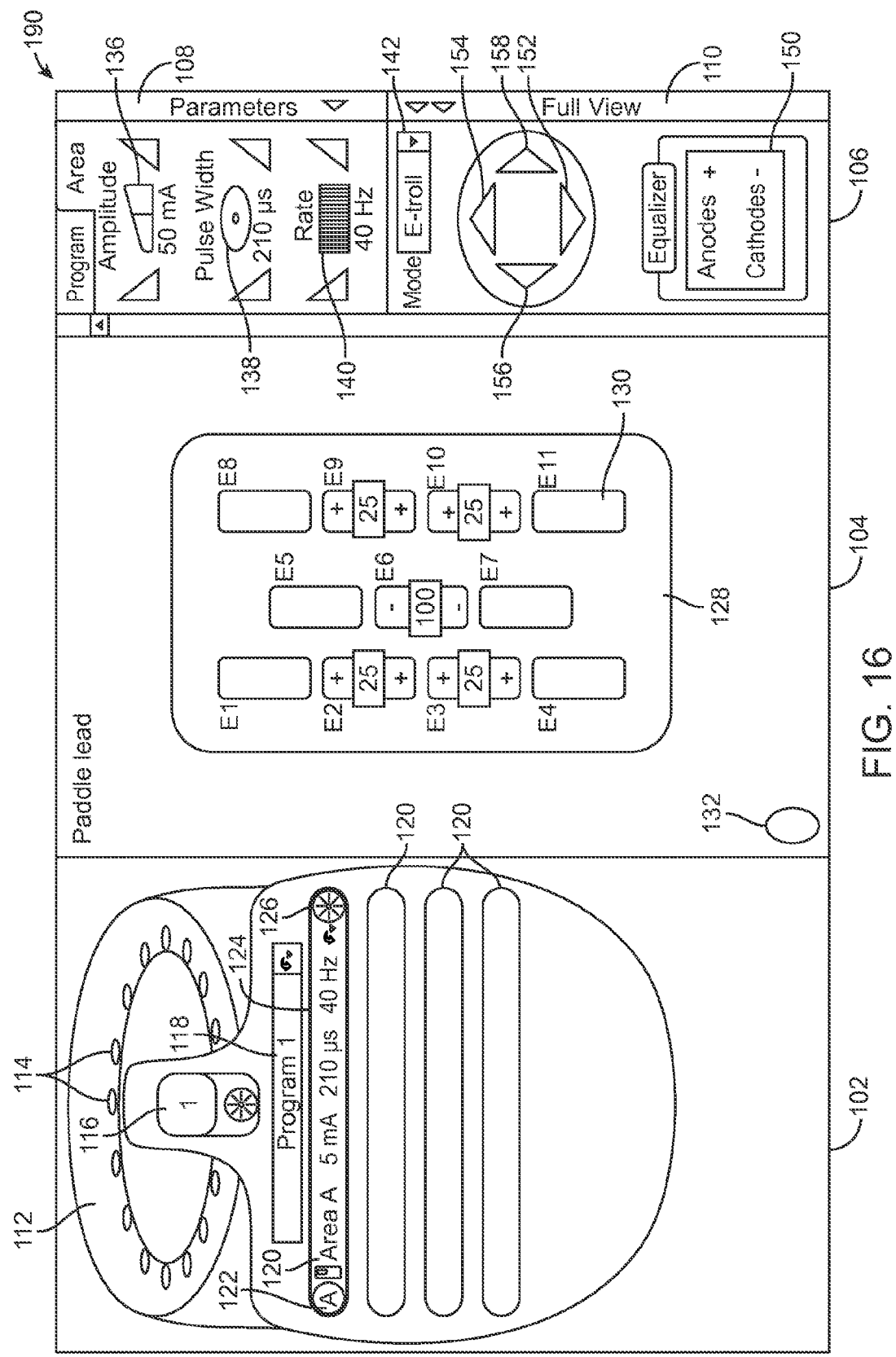
FIG. 16 is a plan view of the user interface in the electronic trolling mode of FIG. 14, particularly showing a third fractionalized electrode configuration.

As shown in FIG. 16, the electrical current is further shifted, such that electrode E6 has a fractionalized cathodic current value of 100%, and electrodes E2, E3, E9 and E10 each have a fractionalized anodic current value of 25%. Further clicking of the down button 152 shifts the cathodic current and anodic current further down the electrode array in a similar manner. Likewise, clicking the up button 154, left button 156, or right button 158 causes the cathodic currents and anodic currents to respectively shift up, left, and right within the electrode array in a similar manner.

As is the case with the manual programming mode, if the longitudinal location of the neurostimulation lead 12 falls between two vertebral levels, the distribution of anodic current around one cathode may be different than the distribution of anodic current around a cathode right below it. For example (not illustrated), supposing the longitudinal location of the neurostimulation lead 12 is such that electrode E5 falls in the cervical region (C1-C7), but electrodes E6 and E7 fall in the lumbar region (T1-T12), the appropriate ratio of stimulation amplitudes between each pair of longitudinal anodes will be 1:1 (as per the exemplary look-up table illustrated in FIG. 9) at the top of the electrode array when fractionalized cathodic current (either 100% or 50%) is allocated to electrode E5, but in moving down the electrode array by clicking the down button 152, the appropriate ratio of stimulation amplitudes between each pair of longitudinal anodes will become 2:1 when 100% of the fractionalized cathodic current is allocated to electrode E6.

It should be appreciated that a steering table is used to generate fractionalized electrode configurations for each neurostimulation lead 12 in the electronic trolling mode. Further details on steering tables are disclosed in U.S. patent application Ser. No. 12/614,942 which has previously been incorporated by reference.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulation system, comprising:
   a neurostimulation lead configured to be implanted along a spinal cord of a patient, the neurostimulation lead including a paddle having a longitudinal axis and an array of electrodes;
   a neurostimulation device configured to deliver electrical stimulation energy to active ones of the electrode array; and
   control/processing circuitry configured to:
      instruct the neurostimulation device to configure an active one of the electrode array as a cathode, and two active ones of the electrode array longitudinally flanking and laterally offset from the cathode as anodes;
      select a ratio of stimulation amplitude values for the two anodes based on a known longitudinal location of the implanted neurostimulation lead relative to the spinal cord; and
      instruct the neurostimulation device to distribute the electrical stimulation energy between the two anodes in accordance with the selected stimulation amplitude value ratio.

2. The neurostimulation system of claim 1, wherein the neurostimulation device is configured to determine the known longitudinal location of the implanted neurostimulation lead relative to the spinal cord.

3. The neurostimulation system of claim 1, further comprising a user interface configured to receive user input defining the known longitudinal location of the implanted neurostimulation lead relative to the spinal cord.

4. The neurostimulation system of claim 1, wherein the control/processing circuitry is configured to:
   select a first ratio of stimulation amplitude values for the two anodes if the known longitudinal location is in a cervical region of the spinal cord; and
   select a second ratio of the stimulation amplitudes for the two anodes if the longitudinal location is in a thoracic region of the spinal cord,
   wherein the first stimulation amplitude ratio is closer to unity than the second stimulation amplitude ratio.

5. The neurostimulation system of claim 4, wherein the control/processing circuitry is configured to determine the more rostral one of the two anodes and the more caudal one of the two anodes, and the stimulation amplitude value for the more rostral anode is greater than the stimulation amplitude value for the more caudal anode.

6. The neurostimulation system of claim 5, wherein the second stimulation amplitude ratio is at least two.

7. The neurostimulation system of claim 1, further comprising memory with a look-up table stored in the memory, the look-up table containing a plurality of different stimulation amplitude ratios and associated neurostimulation lead locations, wherein the control/processing circuitry is configured to select the stimulation ratio amplitude ratio by matching the known longitudinal location of the neurostimulation lead relative to the spinal cord with one of the neurostimulation lead locations stored in the look-up table and selecting the stimulation amplitude ratio associated with the matched neurostimulation lead location.

8. The neurostimulation system of claim 1, wherein the control/processing circuitry configured to:
   instruct the neurostimulation device to configure two other active ones of the electrode array longitudinally flanking and laterally offset from the cathode as anodes;
   select another ratio of stimulation amplitude values for the two other anodes based on the known longitudinal location of the implanted neurostimulation lead relative to the spinal cord; and
   instruct the neurostimulation device to distribute the electrical stimulation energy between the two other anodes in accordance with the other selected stimulation amplitude value ratio.

9. The neurostimulation system of claim 1, wherein the array of electrodes includes electrodes arranged in a plurality of columns extending along the longitudinal axis, the cathode is in a first one of the columns, and the two anodes are in a second one of the columns.

10. The neurostimulation system of claim 1, wherein the control/processing circuitry is contained within the neurostimulation device.

11. The neurostimulation system of claim 1, further comprising an external controller containing the control/processing circuitry.

12. An external controller for use with a neurostimulation device coupled to an array of electrodes arranged along a longitudinal axis of the spinal column of the patient, the external controller comprising:
   a user interface configured to receive user input;
   control/processing circuitry configured to generate a set of stimulation parameters in response to the user input, the stimulation parameter set including an electrode combination designating one of the electrodes as a cathode, and two electrodes longitudinally flanking and laterally offset from the cathode as anodes, the stimulation parameter set further including stimulation amplitude values for the two anodes, the stimulation amplitude values having a ratio based on a known longitudinal location of the implanted neurostimulation lead relative to the spinal cord; and output circuitry configured for transmitting the stimulation parameter set to the neurostimulation device.

13. The external control device of claim 12, wherein the control/processing circuitry is configured to determine the known longitudinal location of the implanted neurostimulation lead relative to the spinal cord.

14. The external control device of claim 12, wherein the user interface is configured to receive additional user input defining the known longitudinal location of the implanted neurostimulation lead relative to the spinal cord.

15. The external control device of claim 12, wherein the control/processing circuitry is configured to:
    select a first ratio of stimulation amplitude values for the two anodes if the longitudinal location is in a cervical region of the spinal cord; and
    select a second ratio of the stimulation amplitudes for the two anodes if the longitudinal location is in a thoracic region of the spinal cord,
    wherein the first stimulation amplitude ratio is closer to unity than the second stimulation amplitude ratio.

16. The external control device of claim 15, wherein the control/processing circuitry is configured to determine the more rostral one of the two anodes and the more caudal one of the two anodes, and the stimulation amplitude value for the more rostral anode is greater than the stimulation amplitude value for the more caudal anode.

17. The external control device of claim 12, further comprising memory storing a look-up table containing a plurality of different stimulation amplitude ratios and associated neurostimulation lead locations, wherein the control/processing circuitry is configured for selecting the stimulation amplitude ratio by matching the known longitudinal location of the neurostimulation lead relative to the spinal cord with one of the neurostimulation lead locations stored in the look-up table and selecting the stimulation amplitude ratio associated with the matched neurostimulation lead location.

18. The external control device of claim 12, wherein the electrode combination further designates two other electrodes longitudinally flanking and laterally offset from the cathode, the stimulation parameter set further including stimulation amplitude values for the two other anodes, the stimulation amplitude values having another ratio based on the known longitudinal location of the implanted neurostimulation lead relative to the spinal cord.

19. The external control device of claim 12, wherein the array of electrodes is arranged in a plurality of columns along the longitudinal axis of the spinal column of the patient, the cathode is in a first one of the columns as a cathode, and the two anodes are in a second one of the columns as anodes.

20. The external control device of claim 19,
    wherein the user interface comprises a directional control device configured to receive the user input;
    wherein the control/processing circuitry is configured to generate a series of sets of stimulation parameters in response to the user input, each of the stimulation parameter sets including an electrode combination designating one of the electrodes in the first electrode column as a cathode, and two electrodes longitudinally flanking the cathode in the second electrode column as anodes, the stimulation parameter set further including stimulation amplitude values for the two anodes, the stimulation amplitude values having a ratio based on a known longitudinal location of the implanted neurostimulation lead relative to the spinal cord; and
    wherein the output circuitry is configured to transmit the stimulation parameter sets to the neurostimulation device.

* * * * *